(12) United States Patent
Mahmood et al.

(10) Patent No.: US 8,423,127 B2
(45) Date of Patent: *Apr. 16, 2013

(54) SYSTEMS AND METHODS FOR GENERATING FLUORESCENT LIGHT IMAGES

(75) Inventors: Umar Mahmood, Winchester, MA (US); Ralph Weissleder, Peabody, MA (US); Rahul A. Sheth, Houston, TX (US); Rabi Upadhyay, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,781

(22) Filed: Oct. 17, 2011

(65) Prior Publication Data

US 2012/0150043 A1    Jun. 14, 2012

Related U.S. Application Data

(62) Division of application No. 11/456,625, filed on Jul. 11, 2006, now Pat. No. 8,078,265.

(51) Int. Cl.
*A61B 6/00* (2006.01)
(52) U.S. Cl.
USPC .......................................................... 600/476
(58) Field of Classification Search ................... 600/476
See application file for complete search history.

(56) References Cited

U.S. PATENT DOCUMENTS 5,347,374 A    9/1994  Fuss et al.
5,363,854 A   11/1994  Martens et al.
5,579,402 A   11/1996  Hayen
5,590,660 A    1/1997  MacAulay et al.
6,148,060 A   11/2000  Collins et al.
6,175,759 B1   1/2001  Chan et al.
6,343,228 B1   1/2002  Qu
6,473,637 B1  10/2002  Hayashi
6,615,063 B1   9/2003  Ntziachristos
6,763,148 B1   7/2004  Sternberg et al.
6,821,245 B2  11/2004  Cline et al.

(Continued)

FOREIGN PATENT DOCUMENTS

EP    1 477 103 A1    11/2004
EP    1 491 133 A1    12/2004

(Continued)

OTHER PUBLICATIONS

Funovics et al.; "Catheter-based in Vivo Imaging of Enzyme Activity and Gene Expression: Feasibility Study in Mice;" Center for Molecular Imaging Research, Massachusetts General Hospital; Radiology, Molecular Imaging, Jun. 2004; pp. 659-666.

(Continued)

*Primary Examiner* — Unsu Jung
*Assistant Examiner* — Saurel J Selkin
(74) *Attorney, Agent, or Firm* — Daly, Crowley, Mofford & Durkee, LLP

(57)    ABSTRACT

An imaging system divides image pixels intensities by exposure time to generate image data in units of intensity per time. The imaging system divides a fluorescent light image in intensity per time units by an excitation light image in intensity per time units to provide a quantitative corrected fluorescent light image that is generally invariant to position of an imaging instrument relative to a biological tissue being imaged.

19 Claims, 15 Drawing Sheets

U.S. PATENT DOCUMENTS

| | | | |
|---|---|---|---|
| 6,899,675 | B2 | 5/2005 | Cline et al. |
| 8,078,265 | B2 | 12/2011 | Mahmood et al. |
| 2003/0135092 | A1 | 7/2003 | Cline et al. |
| 2003/0236458 | A1 | 12/2003 | Hochman |
| 2006/0082845 | A1 | 4/2006 | Watanabe |
| 2008/0312540 | A1 | 12/2008 | Ntziachristos |
| 2011/0087111 | A1 | 4/2011 | Ntziachristos |

FOREIGN PATENT DOCUMENTS

| | | |
|---|---|---|
| EP | 1 637 062 A1 | 3/2006 |
| JP | 5-293108 | 11/1993 |
| JP | 8-89478 | 4/1996 |
| JP | HEI 9-294705 | 11/1997 |
| JP | 2002-301009 | 10/2002 |
| JP | 2005-514147 | 5/2005 |
| WO | WO 95/26673 | 10/1995 |
| WO | WO 2003/009739 A2 | 2/2003 |
| WO | WO 2003/009739 A3 | 2/2003 |
| WO | WO 2006/063246 A2 | 6/2006 |
| WO | WO 2008/008231 | 1/2008 |

OTHER PUBLICATIONS

Funovics et al.; "Miniaturized Multichannel Near Infrared Endoscope for Mouse Imaging;" 2003 Massachusetts Institute of Technology; Molecular Imaging; vol. 2, No. 4; Oct. 2003; pp. 350-357.

Kircher et al.; "A Dual Fluorochrome Probe for Imaging Proteases;" 2004 American Chemical Society; Bioconjugate Chem.; American Chemical Society; vol. 15, No. 2; Feb. 28, 2004; pp. 242-248.

Mahmood et al.; "Feasibility of in Vivo Multichannel Optical Imaging of Gene Expression: Experimental Study in Mice;" Center for Molecular Imaging Research, Massachusetts General Hospital; Radiology; vol. 224, No. 2; Aug. 2002; pp. 446-451.

Mahmood et al.; "Near-Infrared Optical Imaging for Protease Activity for Tumor Detection;" Department of Radiology, Center for Mulocular Imaging Research, Massachusetts General Hospital; Radiiology; vol. 213, No. 3; Dec. 1999; pp. 866-760.

Weissleder et al.; "In Vivo Imaging of Tumors with Protease-Activated Near-Infrared Fluorescent Probes;" 1999 Nature America Inc.; Nature Biotechnology; vol. 17, Apr. 1999; pp. 375-378.

EP Office Action from EP Application No. 07810121.9-2319; dated Jan. 13, 2011; 3 pages.

EP Response to Official Communication; filed on Jun. 28, 2011; for EP Pat. App. No. 07810121.9; 22 pages.

PCT International Preliminary Report on Patentability dated Jun. 21, 2007; of the ISA for PCT/US2005/044651; 9 pages.

PCT Invitation to Pay Additional Fees with Partial Search Report dated Dec. 13, 2007; from the ISA for PCT/US2007/015295; 8 pages.

PCT Search Report and Written Opinion dated Apr. 4, 2008; of the ISA for PCT/US2007/01529; 14 pages.

PCT International Preliminary Report on Patentability dated Jan. 22, 2009; of the ISA for PCT/US2007/015295; 10 pages.

Office Action/Restriction Requirement dated Dec. 14, 2009; for U.S. Appl. No. 11/720,967; 5 pages.

Response filed Jan. 14, 2010; to Office Action/Restriction Requirement dated Dec. 14, 2009; for U.S. Appl. No. 11/720,967; 1 page.

Office Action dated Sep. 20, 2010; for U.S. Appl. No. 11/720,967; 13 pages.

Office Action/Restriction Requirement dated Mar. 6, 2009; for U.S. Appl. No. 11/456,625; 10 pages.

Response filed Apr. 1, 2009; to Office Action/Restriction Requirement dated Mar. 6, 2009; for U.S. Appl. No. 11/456,625; 1 page.

Office Action dated Apr. 16, 2009; for U.S. Appl. No. 11/456,625; 9 pages.

Response filed Sep. 16, 2009; to Office Action dated Apr. 16, 2009; for U.S. Appl. No. 11/456,625; 21 pages.

Final Office Action dated Mar. 24, 2011; for U.S. Appl. No. 11/456,625; 9 pages.

Response filed May 19, 2011; to Final Office Action dated Mar. 24, 2011; for U.S. Appl. No. 11/456,625; 12 pages.

Notice of Allowance dated Jul. 22, 2011; for U.S. Appl. No. 11/456,625; 7 pages.

EP Official Communication dated Mar. 5, 2012; for EP Pat. App. No. 07810121.9; 3 pages.

EP Official Communication dated Oct. 4, 2012; for EP Pat. App. No. 05 853 540.2-2035; 3 pages.

Response to EP Official Communication dated Mar. 5, 2012; for EP Pat. App. No. 07 810 121.9; 2 pages.

Japanese Office Action; received Nov. 16, 2012; for JP Pat. App. No. 2007-545669; 6 pages.

PCT Search Report and Written Opinion of the ISA for PCT/US2005/044651 dated Apr. 25, 2006; 14 pages.

U.S. Appl. No. 11/720,967; 405 pages.

European Office Action; dated Oct. 4, 2012; for EP Pat. App. No. 05 853 540.2; 3 sheets.

PCT International Preliminary Report on Patentability of the ISA; dated Jun. 21. 2007; for PCT Pat. App. No. PCT/US2005/044851; 9 pages.

EP Official Communication dated Jan. 13, 2011; for EP Pat. App. No. EP 07 810 121.9; 3 sheets.

EP Response to Official Communication dated Jun. 21, 2011; for EP Pat. App. No. 07801021.9; 22 pages.

Transmittal of Japanese Notce of Rejection; dated Oct. 26, 2012; for JP Pat. App. No. 2009-519457; 4 sheets.

Letter from Yuasa and Hara; dated Jan. 16, 2013; for Japanese Patent Application No. 2009-519457; 3 pages.

Letter to Yuasa and Hara; dated Jan. 21, 2013; for Japanese Patent Application No. 2009-519457; 2 pages.

Letter from Yuasa and Hara; dated Feb. 20, 2013; for Japanese Patent Application No. 2009-519457; 9 pages.

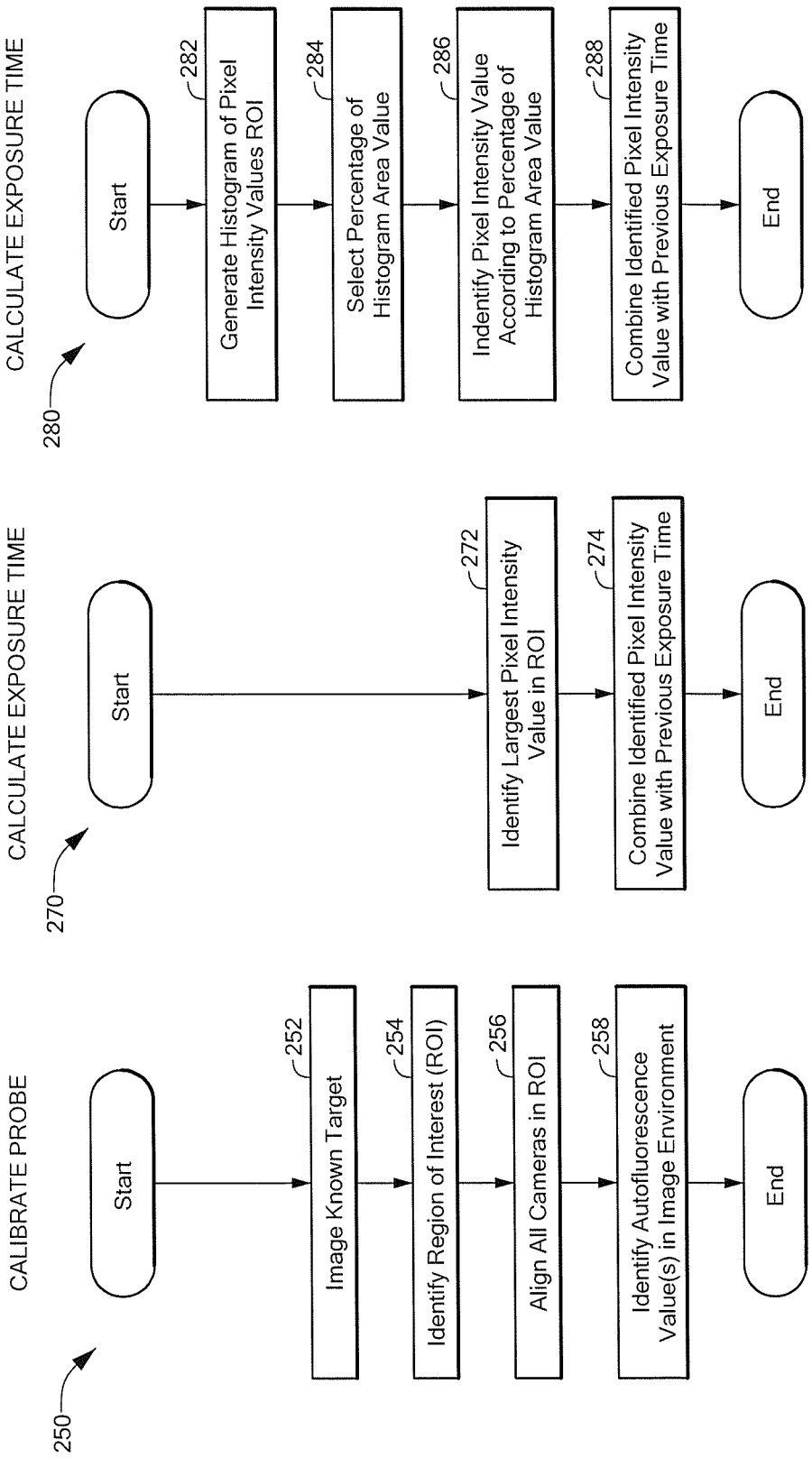

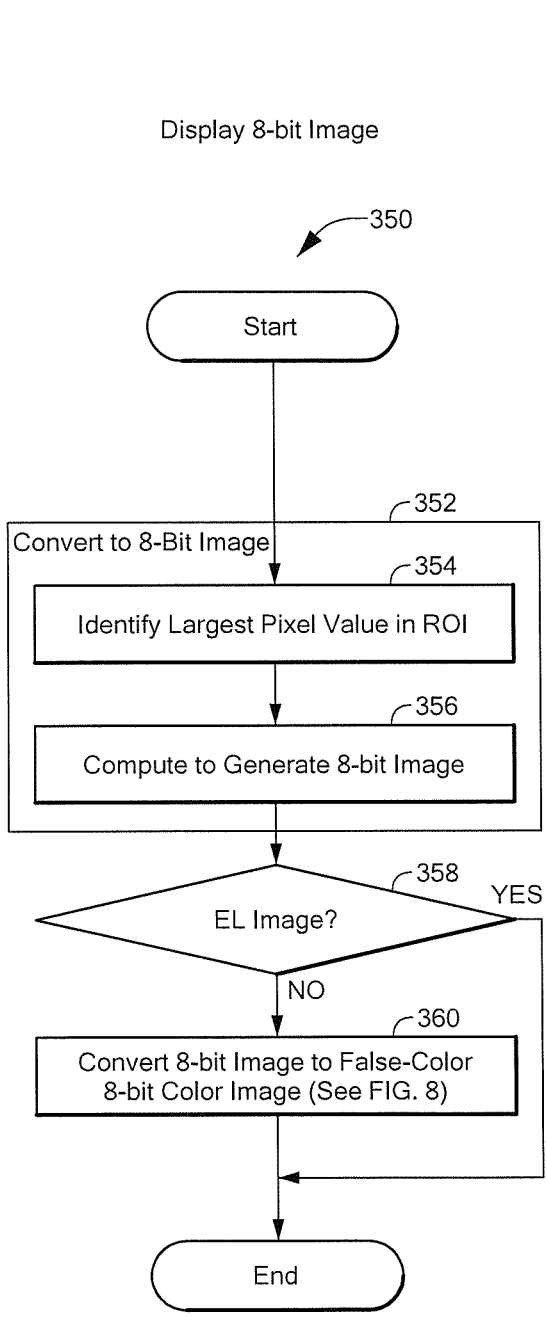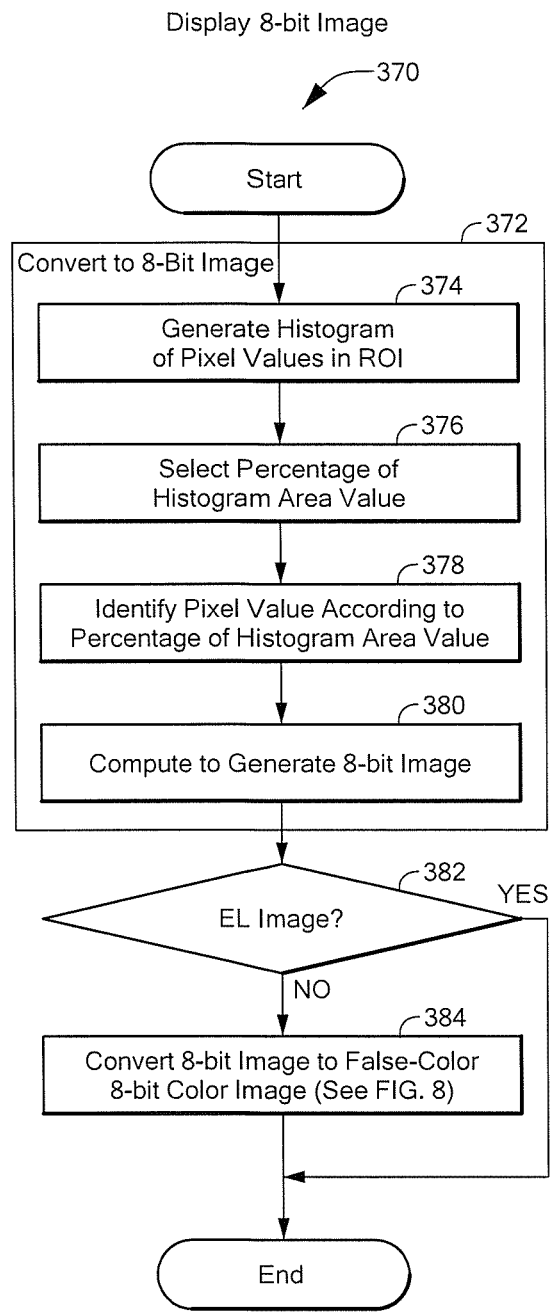
*FIG. 7*  *FIG. 7A*

SYSTEMS AND METHODS FOR GENERATING FLUORESCENT LIGHT IMAGES

CROSS REFERENCE TO RELATED APPLICATIONS

This application is a Divisional Application of and claims the benefit of and priority to U.S. patent application Ser. No. 11/456,625, filed on Jul. 11, 2006 now U.S. Pat. No. 8,078,265, which application is hereby incorporated herein by reference in their entirety.

STATEMENT REGARDING FEDERALLY SPONSORED RESEARCH

This invention was made with government support under Contract No. RO1-EB001872 awarded by the National Institute of Health. The government has certain rights in the invention.

FIELD OF THE INVENTION

This invention relates generally to imaging systems and methods and, more particularly, to optical imaging systems and methods adapted to provide fluorescent light images of biological tissue.

BACKGROUND OF THE INVENTION

Conventionally, fluorescent light has been used to generate microscopic images of histological slices of biological tissue using so-called fluorescence microscopy. However, tissue sectioning used in conventional fluorescence microscopy is limited to slice thicknesses (i.e., tissue depths) on the order of half a millimeter, and therefore, conventional fluorescence microscopy is not appropriate for imaging through entire organs or through the whole human body.

In order to provide images deeper into tissue, conventional systems and techniques have used light sources and fluorochromes that emit near infrared light. The near infrared light is selected because near infrared light has low absorption and can penetrate several centimeters into biological tissue. Near infrared light is used in a variety of optical imaging systems and techniques.

Fluorescent light can be emitted from a tissue in response to an excitation light source transmitting excitation light into the tissue. The excitation light excites the emission of fluorescent light from fluorochromes, some of which are man-made molecules, within the tissue. The excitation light can also excite the emission of fluorescent light from fluorescent proteins within the tissue, including fluorescent proteins that do not naturally occur within tissue. The excitation light can also excite the emission of fluorescent light from naturally occurring molecules within the tissue, generating so-called autofluorescence.

Fluorescence reflectance imaging (FRI) is a conventional technique used to generate microscopic and macroscopic images of fluorescent light emitted by a biological tissue. An FRI system transmits light onto and/or into biological tissue and collects fluorescence light that is emitted back from the tissue. In fluorescence reflectance imaging, excitation light (for example, near-infrared light) from an excitation light source is used to illuminate the tissue. In some existing systems, the excitation light source is used to excite exogenously administered fluorochromes within the tissue that, in turn, emit fluorescent light. Alternatively, in some existing systems the excitation light source is used to excite naturally occurring fluorogenic molecules (i.e., resulting in autofluorescence) within the tissue that emits fluorescent light. The emitted fluorescent light can be visually inspected or it can be captured with a CCD camera or other photon detector positioned generally on the same side of the tissue as the excitation light source.

Fluorescence transillumination imaging (FTI) is another conventional technique used to generate macroscopic images of fluorescent light emitted by a biological tissue. As with FRI, in FTI, excitation light (for example, near infrared light) from an excitation light source is used to illuminate a tissue, and the excitation light propagates into the tissue, exciting the emission of fluorescent light from within the tissue. However, in contrast to the above-described fluorescence reflectance arrangement, in fluorescence transillumination imaging, a CCD camera or other photon detector is positioned generally on the opposite side of the tissue from the excitation light source. In some arrangements, the emitted fluorescent light is near infrared light.

Fluorescence reflectance imaging (FRI) and fluorescence transillumination imaging (FTI) are forms of "planar" imaging, which provide two-dimensional images. More advanced optical imaging systems and methods have been developed, which utilize tomographic methods. These systems and methods operate by obtaining photonic measurements at different projections (i.e., angles) to the tissue and combining the measurements using a tomographic algorithm. Advantages of tomography include an ability for image quantification of deep fluorochromes, and an ability to provide three-dimensional imaging with feature depth measurements. In some applications, tomography has been used in-vivo to measure enzyme regulation and treatment response to drugs. However, tomography is more complex than planar imaging, requiring more advanced instrumentation, requiring multiple illumination points (projections), which can require multiple light sources, and requiring advanced theoretical methods for modeling photon propagation in tissues.

Some fluorescence imaging systems use a catheter-based or an endoscopic arrangement, wherein an excitation light source and a light receiver are coupled via fiber-optic bundle to a catheter-based or endoscopic instrument (hereafter referred to as an insertable instrument), which can be inserted, for example, within a body cavity, organ, or vessel.

The insertable instruments have resolved some of the imaging depth limitations of the above described fluorescence reflectance imaging by allowing intravital access to pathologies deeper inside the body, such as bladder cancer, ovarian cancer, lung cancer, bronchial cancer, and colonic polyps and cancer, as well as arterial plaque. However, with the above-described insertable arrangement, it can be recognized that, as the insertable instrument is moved within the body, the fluorescent light in each image will vary, because the distance from the insertable instrument to the tissue and the angle relative to a surface of the tissue being imaged can vary greatly, making quantifiable assessment of fluorescence difficult from image to image. Variable distances and angles of the insertable instrument during image acquisition result in variable light paths for each image frame, both for excitation light traveling to the tissue and for emission light traveling back to the insertable instrument. Different light paths, in turn, cause different levels of light at an image recording device, and ultimately result in variable signal intensities in each image as images are collected in real time. The variable intensities in each image make it difficult to compare images as they are sequentially captured.

Conventional insertable arrangements are also limited to 8-bit dynamic range for each of two or three optical channels (e.g., a channel to form an image of the excitation light, and one or two channels to form images of fluorescent light).

In general, an intensity of fluorescent light received from a biological tissue is indicative of a concentration of fluorescent molecules within the biological tissue. However, since conventional insertable arrangements have limited ability to provide a quantifiable and correct intensity of images in the various collected images as the insertable instrument is moved about, it is not generally possible in conventional insertable arrangements to determine concentrations of fluorescent light generating molecules in the tissue or to provide an image indicative of the concentrations in real-time.

SUMMARY OF THE INVENTION

The present invention provides improved fluorescence images when used with an insertable optical instrument. However, the systems and techniques described herein are applicable to any fluorescence imaging system, including fluorescence imaging systems that do not include an insertable instrument.

Examples of fluorescence reflectance imaging are used herein to describe the systems and techniques of the present invention. However, it should be recognized that the systems and techniques described herein can also be applied to fluorescence transillumination imaging.

As described below, in accordance with some aspects of the present invention, an imaging system can provide images of an object that are quantitatively indicative of concentration of a fluorescent substance, which images can be collected and viewed in real time. The indication of the concentration of the fluorescent substance can be generally invariant with respect to a distance and an angle of an insertable instrument relative to the object.

In accordance with an aspect of the present invention, an imaging system includes an image capture processor adapted to capture a plurality of images from a light detector. Each image within the plurality of images has a respective exposure time. The image capture processor includes an exposure processor adapted to dynamically adjust the respective exposure times associated with each image within the plurality of images. The imaging system further includes a memory coupled to the image capture processor and adapted to receive and store the plurality of images and adapted to receive and store the respective exposure times.

In accordance with another aspect of the present invention, an imaging system includes an excitation light source adapted to direct excitation light at a tissue and adapted to excite fluorescent light from the tissue. The imaging system further includes a first light detector adapted to generate a first image of the tissue having a first plurality of pixel intensity values associated with a first exposure time and a second light detector adapted to generate a second image of the tissue having a second plurality of pixel intensity values associated with a second exposure time. The imaging system further includes an image correction processor coupled to the first and second light detectors and to the excitation light source. The image correction processor is adapted to combine each one of the first pixel intensity values with the first exposure time to provide first combined intensity values, adapted to combine each one of the second pixel intensity values with the second exposure time to provide second combined intensity values, and adapted to combine the second intensity-per-second values with the first intensity-per-second values to provide a corrected image of the tissue having corrected pixel intensity values.

In accordance with another aspect of the present invention, an imaging system includes an image re-scaling processor adapted to receive a plurality of images. Each image within the plurality of images has respective pixel intensity values consisting of a first number of digital bits. The image re-scaling processor is further adapted to convert, concurrently with receipt of each image within the plurality of images, each one of the images to a respective image having respective pixel intensity values consisting of a second different number of digital bits.

In accordance with another aspect of the present invention, an imaging system includes an imaging processor. The imaging processor includes an intensity-to-concentration mapping processor adapted to generate a map of pixel intensity values (corrected for exposure time) to respective concentrations of a chemical compound within a tissue. The imaging processor further includes an image coloring processor coupled to the image-to-intensity mapping processor and adapted to apply the map to a grayscale image to generate a false color image according to the concentrations, concurrently with receipt of the grayscale image. The mappings performed by the imaging processor can be quantitative, meaning that the intensity-to-concentration mapping and intensity-to-color mapping are invariant over changes in distance or angle between the optical imaging instrument and the target being imaged.

In accordance with another aspect of the present invention, an imaging system includes an imaging processor adapted to generate an image of light emitted by or reflected from a tissue. The imaging processor includes an image combining processor adapted to receive a secondary image from another type of imaging system and to combine the image of light with the secondary image to provide a combined image, concurrently with the generation of the image of light.

BRIEF DESCRIPTION OF THE DRAWINGS

The foregoing features of the invention, as well as the invention itself may be more fully understood from the following detailed description of the drawings, in which:

FIG. 4 is a flow chart showing an instrument calibration process, which is indicative of further details of the process of FIG. 3;

FIG. 5 is a flow chart showing an exposure time calculation process, which is indicative of further details of the process of FIG. 3

FIG. 5A is a flow chart showing another exposure time calculation process, which is indicative of further details of the process of FIG. 3 as an alternative to the process of FIG. 5;

FIG. 7 is a flow chart showing an image resolution conversion process, which is indicative of further details of the process of FIG. 3;

FIG. 7A is a flow chart showing another image resolution conversion process, which is indicative of further details of the process of FIG. 3 as an alternative to the process of FIG. 7;

FIG. 9A is an image of an exemplary segmentation mask;

DETAILED DESCRIPTION OF THE INVENTION

Figure 1:
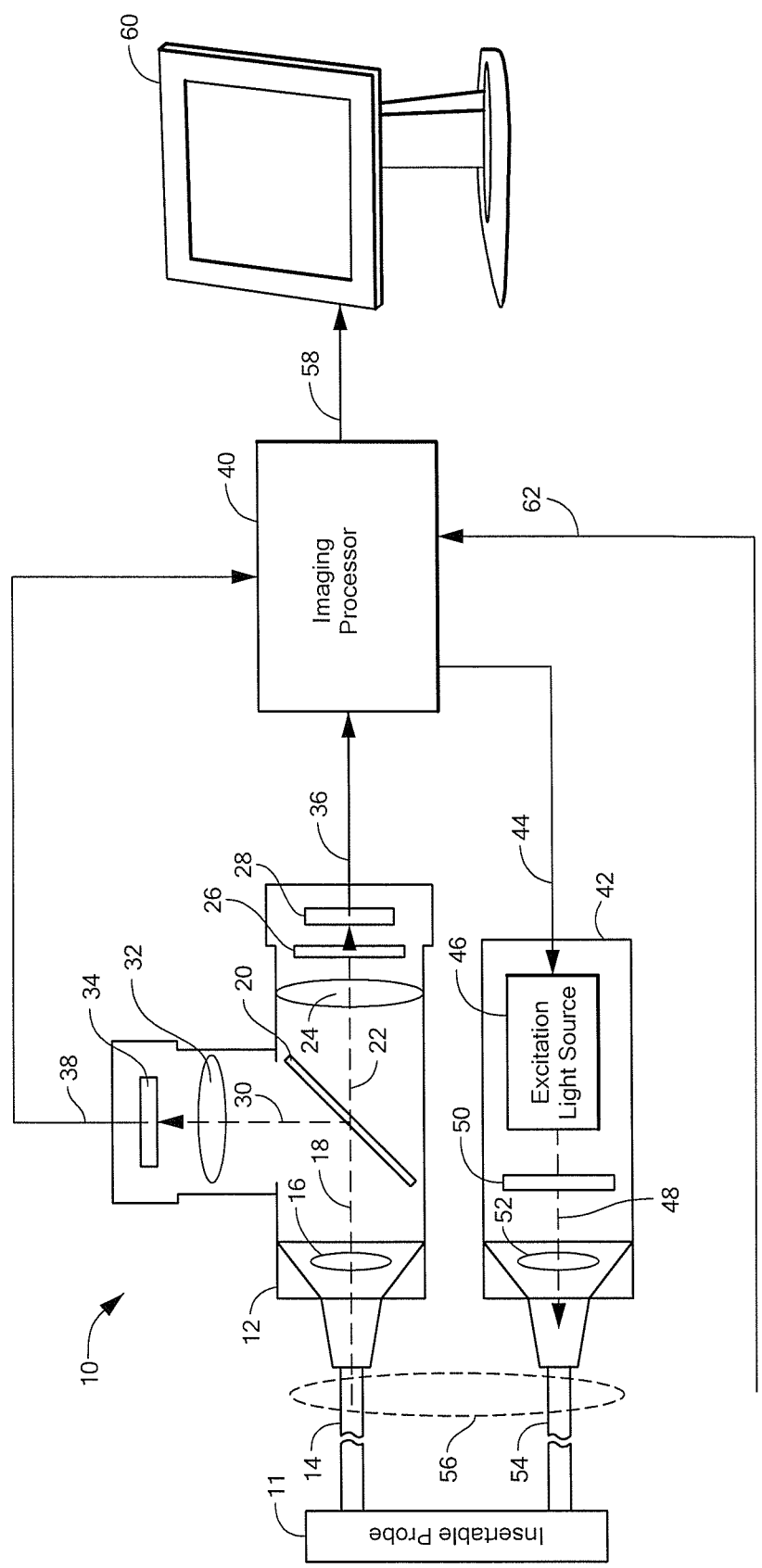
FIG. 1 is a block diagram showing a fluorescence imaging system having an imaging processor.

Before describing the present invention, some introductory concepts and terminology are explained. As used herein, the term "excitation light" is used to describe light generated by an excitation light source. The excitation light includes, but is not limited to, spectral light components (i.e., wavelengths) capable of exciting fluorescence from a biological tissue. The spectral components in the excitation light that are capable of exciting fluorescent light can include a single wavelength, a single band of wavelengths, more than one wavelength, or more than one spectral band of wavelengths. The spectral components in the excitation light that are capable of exciting fluorescent light can include one or more wavelengths in the visible spectral regions of about 400 to 700 nanometers. However, the spectral components in the excitation light that are capable of exciting fluorescent light can also include one or more wavelengths in the other spectral regions, for example, in the near infrared (NIR) spectral region of about 700 to 1000 nanometers, or in the ultra-violet (UV) spectral region of about 1 to 400 nanometers. The excitation light can also include spectral components that do not excite fluorescent light.

In some embodiments, the excitation light is coherent light, e.g., laser light. In other embodiments, the excitation light is incoherent light, e.g., photons generated from an LED or filtered light generated from black body radiation (e.g. incandescent, halogen, or xenon bulb). In other embodiments, the excitation light is a combination of coherent and incoherent light.

The spectral components of the excitation light that are capable of exciting fluorescent light can have wavelengths shorter than the fluorescent light that they excite. However, in other arrangements, some additional spectral components of the excitation light can have wavelengths longer than the fluorescent light that they excite.

As used herein, the terms "fluorescence" and "fluorescent light" are used to described light that emanates from a biological tissue. The fluorescent light can be generated either by man-made molecules, for example, exogenous fluorochromes (also referred to as "fluorescent probes," or simply "probes"), by fluorescent proteins such as green fluorescent protein, or by naturally occurring molecules resident within or placed within the biological tissue. When generated by endogenous, naturally occurring molecules, the fluorescent light can be referred to as "autofluorescent light" or "autofluorescence."

In general, the fluorescent light is generated in the biological tissue in response to the excitation light having the above-described spectral components capable of exciting the fluorescent light. The fluorescent light can include a single wavelength, a single band of wavelengths, more than one wavelength, or more than one spectral band of wavelengths. The fluorescent light can include one or more wavelengths in the visible spectral regions of about 400 to 700 nanometers. However, the fluorescent light can also include one or more wavelengths in the other spectral regions, for example, in the near infrared (NIR) spectral region, or in the ultra-violet (UV) spectral region.

As used herein, the term "insertable instrument" is used to describe an optical instrument that can be inserted into the body of a patient. The insertable instrument can be in a variety of forms. For example, the insertable instrument can be a fiber optic endoscope, which is inserted into the body. For another example, the insertable instrument can be a catheter that has a fiberoptic bundle as well as one or more "working channels" that allow the passage of biopsy tweezers, saline, air, etc. through the catheter tip. For another example, the insertable instrument can also be a tube in which a number of optical lenses are present (borescope). In general, the insertable instrument is coupled by way of a fiber-optic bundle or lenses to a light transmitter and a light receiver, described more fully below. Therefore, the insertable instrument can be part of a system that can provide optical views inside of the patient. As used herein, a "distal end" of the fiber-optic bundle is an end of the bundle furthest from the insertable instrument, and a "proximal end" of the fiber-optic bundle is an end of the bundle nearest the insertable instrument. The insertable instrument can also refer to devices in which the entire focusing element and recording element are inside the patient, for example, hand held devices in which the recording device is attached to the focusing element directly.

The term "imaging instrument" is used herein to describe not only the above-descried insertable instrument, but also instruments that are not inserted into the body. The imaging instrument is disposed at the proximal end of the fiber optic bundle or light transmitting guide.

As used herein, the term "fluorochrome" is used to describe a family of compounds or molecules that emit fluorescent light in response to an excitation light. Useful fluorochromes are those that can be disposed in or on biological tissue and that tend to concentrate at (or disperse from) sites of particular biological features, for example, at a tumor, or at sites of particular biological functions.

As used herein, the term "fluorescence reflectance imaging" or "FRI" apply to both fluorescence imaging of a surface of a biological tissue and also to fluorescence imaging below a surface of a biological tissue, i.e., within the biological tissue.

While discussion and examples below describe imaging of a biological tissue, other objects or materials can also be imaged according to the system and techniques described below. Other objects include, but are not limited to, a liquid, for example, blood, and a gas. Additionally, surfaces of materials used in construction and manufacture could be evaluated for quantitative fluorescence properties using the methods described in this application.

As will become apparent from discussion below, in accordance with some aspects of the present invention, an imaging system can provide fluorescence images of an object, e.g., a biological tissue, which fluorescence images can be collected and viewed in real time. The fluorescence images can have intensities that are generally invariant with respect to a distance and an angle of an imaging instrument relative to the object.

As will also become apparent from discussion below, in accordance with some other aspects of the present invention, an imaging system can provide images of an object that are quantitatively indicative of concentration of a fluorescent substance (e.g., by way of colors), which images can be collected and viewed in real time. The indication of the concentration of the fluorescent substance (e.g., the colors) can be generally invariant with respect to a distance and an angle of an imaging instrument relative to the object. Such images are referred to as "quantitative" images herein.

Referring now to FIG. 1, an imaging system 10 can include a light receiver 12 coupled through an optical fiber 14 to an insertable instrument 11. The light receiver 12 is optically coupled to receive light 18 from the optical fiber 14. The light receiver 12 can include one or more receiving lenses, for example, a lens 16, which is optically coupled between the optical fiber 14 and a light splitting element 20. The light splitting element 20 can be in the form of, but is not limited to, a dichroic mirror or a prism. The light receiver 12 can also include another lens 24 optically coupled between the light splitting element 20 and an optical filter 26. A charge coupled device (CCD) 28 can be optically coupled to the optical filter 26. The light receiver 12 can still further include yet another lens 32 optically coupled between the light splitting element 20 and another charge coupled device 34.

It will be understood that the charge coupled devices 28, 34 may have associated electronics (not shown) to generate the image data 36, 38, respectively. Therefore, the CCDs 28, 34 may be described as CCD cameras, or more generally, as "light detectors." In one particular embodiment, the CCD 28 is Pixelfly QE camera having a grayscale CCD and the CCD 34 is a Pixelfly SVGA camera with a color CCD, which are each manufactured by PCO AG of Kelheim, Germany. Each of these particular cameras generates image data having twelve bits, with a sixteen-bit data transfer.

In one particular embodiment, the lenses 16, 24 are achromatic lenses with respective focal length of fifty millimeters. In one particular embodiment, the optical filter is a band pass optical filter with a pass band centered on a spectral peak of the fluorescent light emanating from the biological tissue being imaged.

In operation of the light receiver 12, the charge coupled device (CCD) 28 generates image data 36 (which can include pixel intensity values), which can, for example, be fluorescent light image data associated with an image of fluorescent light. In operation, the charge coupled device 34 generates image data 38, which can, for example, be excitation light image data associated with an image of excitation light.

The light receiver 12 is coupled to an imaging processor 40, which is adapted to combine the image data 36 and the image data 38 and to generate "corrected" image data 58, which is corrected at least with regard to the above described variable intensities resulting from movement of the insertable instrument 11 relative to a biological tissue being imaged. It should be recognized that each one of the CCDs 28, 34 can have a different respective acquisition time and exposure time. Furthermore, each individual image can have a different respective acquisition time and exposure time. Therefore, it may not be possible to directly compare the images represented by the image data 36 with the images represented by the image data 38 without intermediate processing before the comparing takes place. The intermediate processing and the comparing or combining of images is described below in conjunction with FIGS. 3, 6, and 6A.

The imaging processor 40 is also adapted to communicate the corrected image data 58 to a display device 60. The corrected image data 58 can be generated substantially concurrently with generation of image data 36, 38 by the charge coupled devices 28, 34 resulting in a real-time display upon the display device 60.

The imaging processor 40 can also be adapted to receive image data 62 from one or more other imaging systems. The other imaging systems can include, but are not limited to a magnetic resonance imaging system, a computer tomography system, an x-ray system, a fluoroscopy system, or a positron emission tomography system. The imaging processor 40 is adapted to combine corrected image data with the image data 62, to provide a display of combined images. For example, the display of combined images can include an overlay of the corrected image data upon the image data 62, or vice versa.

The imaging system 10 can still further include a light transmitter 42 coupled though an optical fiber 54 to the insertable instrument 11. In some arrangements, the two optical fibers 14, 54 can be co-located in a single fiber-optic bundle 56. In some arrangements one or both to the optical fibers 14, 54 can be comprised of a plurality of optical fibers.

In one particular embodiment, the fiber optic bundle 56 is within a 1.6 mm diameter catheter having the optical fiber 14 internally disposed and having the optical fiber 54 externally disposed, as made by Edwards LifeSciences of Irvine, Calif. The catheter can also have a 0.9 mm diameter instrument channel and a working length of about 100 cm.

The light transmitter 42 can include an excitation light source 46 optionally coupled to the imaging processor 40. The light transmitter 42 can also include an optical filter 50, which can be optically coupled between a lens 52 and the excitation light source 46. The lens 52 can be optically coupled to the optical fiber 54. In one particular embodiment, the excitation light source can be a 300 watt xenon lamp (Sunoptics, Jacksonville, Fla.) and the optical filter 50 can be a 680 nm long-pass filter, which tends to decrease heat output and decrease a false-positive fluorescent light signal.

In further operation of the light receiver 12, a light signal 18 is received from the fiber optic cable 14. The light signal 18 can be comprised of a combination of excitation light that has reflected from a biological issue and also fluorescent light that has emanated from the biological tissue. However, in some arrangements, for which the excitation light source is strobed on and off, at one time, the light signal 18 can be comprised of excitation light that has reflected from a biological issue and also fluorescent light that has emanated from the biological tissue, and at another time, when the excitation light source is strobed off, the light signal 18 can be comprised primarily of fluorescent light that has emanated from the biological tissue.

The light signal 18 is split into two light signals 22, 30 by the light splitting element 20. The light signals 22, 30 can have all of or only some of spectral components of the light signal 18, depending upon characteristics of the light splitting device 20.

The light signal 22 can pass through the optical filter 26, which can provide filtering so that only fluorescent light, which is excited by the excitation light 48, and which has a particular wavelength, and/or a particular band of wavelengths, impinges upon the charge coupled device 28. Therefore, the image data 36 is representative of a fluorescent light image.

The light signal 30, which does not pass through an optical filter, and which is representative of the excitation light 48 having reflected from the biological tissue, impinges upon the charge coupled device 34. Therefore, the image data 38 is representative of an excitation light image.

In operation of the light transmitter 42, the excitation light source 46 can, in some embodiments, generate the excitation light 48 continuously, so that it is on both while an excitation light image is captured and while a fluorescent light image is captured. However, in other arrangements, the excitation light source 46 can generate the excitation light 48 intermittently in response to a control signal 44 provided by the imaging processor 40, and/or the excitation light 48 can be varied in intensity in response to the control signal 44. In some arrangements, the excitation light source 46 is turned on while an excitation light image is captured, and it is turned off while a fluorescent light image is captured. The excitation light 48 passes through the (optional) optical filter 50, resulting in the excitation light 48 having selected spectral characteristics.

As described above, the excitation light 48 can be coherent light, incoherent light, or a combination of coherent and incoherent light. At least a spectral portion of the excitation light 48 is selected to excite fluorescence within a biological issue.

While one light signal 22 for generating image data 36 representative of one fluorescent light image is shown, it should be understood that, in other optical arrangements, further light paths can be provided by the light receiver 12, each passing through different respective optical filters comparable to the optical filter 26, but each having different respective pass bands, and each impinging upon a different respective charge coupled device, comparable to the charge coupled device 28. With these arrangements, a plurality of image data can be generated, comparable to the image data 36, but each image data representative of a fluorescent light image at a different light wavelength. Therefore, different fluorescence properties of a biological tissue can be viewed simultaneously or one at a time in real-time.

Figure 2:
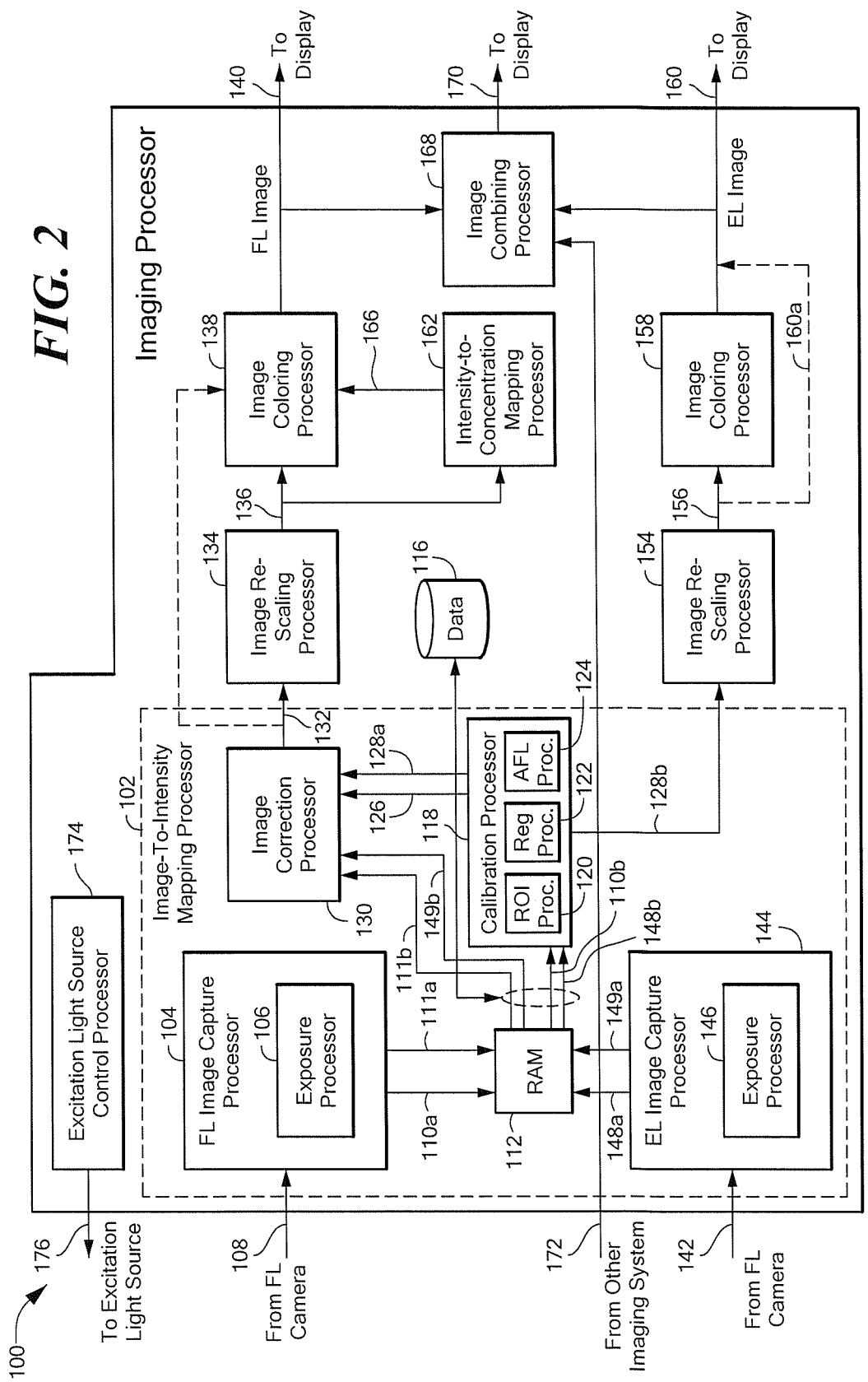
FIG. 2 is a block diagram showing further details of the imaging processor of FIG. 1.

Referring now to FIG. 2, an imaging processor 100 can be the same as or similar to the imaging processor 40 of FIG. 1. The imaging processor 100 can include an image-to-intensity mapping processor 102, which, in turn can include a fluorescent light (FL) image capture processor 104.

The FL image capture processor 104 is adapted to receive image data 108 (see image data 36 of FIG. 1) from a light receiver, for example, from the light receiver 12 of FIG. 1. In some arrangements, the light receiver is in the form of a camera, characterized by having a charge coupled device responsive to fluorescent light, i.e., a fluorescent light (FL) camera.

The FL image capture processor 104 can include an exposure processor 106, which can be adapted to control the exposures of the images represented by the image data 108. Exposure control is further described below in conjunction with FIGS. 3, 5, and 5A. The FL image capture processor 104 generates exposure controlled FL image data 110a accordingly, which is representative of exposure-controlled images of fluorescent light. The FL image capture processor 104 also generates exposure time data 111a, representative of respective exposure times associated with each one of the images of fluorescent light represented by the FL image data 110a.

A random access memory (RAM) 112 is adapted to receive the exposure controlled FL image data 110a and the associated exposure time data 111a, and to provide the exposure controlled FL image data 110b to a calibration processor 118. The exposure controlled FL image data 110b and the associated exposure time data 111b can also be provided to a storage device 116, for example, a disk drive, for archiving and later retrieval.

The calibration processor 118 can include a region of interest (ROI) processor 120 adapted to select, from the exposure controlled FL image data 110b, FL image data that is within a region of interest within an image represented by the exposure controlled FL image data 110b. The region of interest is further described below in conjunction with FIGS. 9 and 9A.

The calibration processor 118 can also include a registration (Reg) processor 122 adapted to align in translation and rotation, and also to scale in an imaging plane, a plurality of FL images represented by the exposure controlled FL image data 110b. In one particular embodiment, the registration processor 122 uses a six-parameter affine transformation to align the plurality of images.

The calibration processor 118 can also include an autofluorescence processor adapted to remove an autofluorescence signal from the exposure controlled FL image data 110b. Removal of the autofluorescence signal is further described below in conjunction with FIGS. 6 and 6A.

The image-to-intensity mapping processor 102 can also include an excitation light (EL) image capture processor 144. The EL image capture processor 144 is adapted to receive EL image data 142 (see image data 38 of FIG. 1) from a light receiver, for example, from the light receiver 12 of FIG. 1. In some arrangements, the light receiver is in the form of a camera, characterized by having a charge coupled device responsive to the excitation light, i.e., an excitation light (EL) camera.

The EL image capture processor 144 can include an exposure processor 146, which can be adapted to control the exposures of the images represented by the EL image data 142. Exposure control is further described below in conjunction with FIGS. 3, 5, and 5A. The EL image capture processor 144 generates exposure controlled EL image data 148a accordingly, which is representative of exposure-controlled images of excitation light. The EL image capture processor 144 also generates exposure time data 149a, representative of respective exposure times associated with each one of the images of excitation light represented by the EL image data 148a.

The random access memory (RAM) 112 is further adapted to receive the exposure controlled EL image data 148a and the associated exposure time data 149a, and to provide the exposure controlled EL image data 148b to the calibration processor 118. The exposure controlled EL image data 148b and the associated exposure time data 149b can also be provided to the storage device 116 for archiving and later retrieval if desired.

The region of interest (ROI) processor 120 is further adapted to select, from the exposure controlled EL image data 148b, EL image data that is within a region of interest within an image represented by the exposure controlled EL image data 148b.

The registration (Reg) processor 122 is further adapted to align in translation and rotation, and also to scale in an imaging plane, a plurality of EL images represented by the exposure controlled EL image data 148b. In one particular embodiment, the registration processor 122 uses an affine transformation to align the plurality of images. The EL images can be so aligned with the FL images described above.

The calibration processor 118 provides calibrated FL image data 126 and calibrated EL image data 128a to an image correction processor 130. The image correction processor 130 is also adapted to receive the exposure time data 111b and the exposure time data 149b, which can be the same as or similar to the exposure time data 111a, 149b, respectively. The image correction processor is adapted to combine the calibrated FL image data 126, the associated exposure time data 111b, the calibrated EL image data 128, and the associated exposure time data 149b, resulting in corrected image data 132.

In some embodiments, the calibrated FL image data 126 is representative of gray scale FL images and the calibrated EL image data 128a is representative of color EL images. Therefore, in order to combine the calibrated FL image data with the calibrated EL image data 128a, the image correction processor can first convert the calibrated EL image data 128a so that it is representative of gray scale EL images. For example, one or more sets of red-green-blue (RGB) pixel intensities can be combined to provide one or more corresponding sets of gray scale intensities. In other embodiments, the calibrated EL image data 128a is already representative of gray scale EL images, and therefore, no color to gray scale conversion needs to be done.

The corrected image data 132 is representative of fluorescence images that are at least corrected to account for the above described under and over exposures associated with conventional imaging systems that use an insertable imaging instrument having variable distance and angle relative to a biological tissue being imaged. This desirable image correction is described in greater detail below in conjunction with FIGS. 3, 11-11C and 12-12C.

An image re-scaling processor 134 is adapted to receive the corrected image data and to provide re-scaled image data 136. In one particular arrangement, the corrected image data 132 is comprised of image data having twelve bits and the re-scaled image data 136 is comprised of image data having eight bits. However, other numbers of bits can also be used.

An image coloring processor 138 is adapted to receive the re-scaled image data 136, which is representative of a gray scale FL image, and to artificially color the re-scaled FL image data 136 to provide artificially colored FL image data 140. The coloring provided by the image coloring processor 138 can be provided in a variety of ways. For example, in one particular embodiment, the image coloring is predetermined such that pixel gray scale intensities in the re-sealed image data 136 are assigned to predetermined colors according to pixel intensity, or ranges of pixel intensities.

However, in other embodiments, the image coloring processor 138 can use color mapping information 166 provided by an intensity-to-concentration mapping processor 162. With this arrangement, the artificially colored FL image data 140 can have colors according to fluorescent light generating molecule concentrations within the biological tissue being imaged. To this end, the intensity-to-concentration mapping processor 162 a process described below in conjunction with FIG. 8 can provide a map of pixel intensities to concentrations before the imaging of the biological tissue begins.

The calibration processor 118 can also provide calibrated EL image data 128b to another image re-scaling processor 154. The calibrated EL image data 128b can be the same as or similar to the calibrated EL image data 128a. The image re-scaling processor 154 operates in substantially the same way as described above in conjunction with the image re-scaling processor 134 to provide re-scaled EL image data 156. In some arrangements, as described above, the calibrated EL image data 128b (and the re-scaled EL image data 156) is representative of gray scale images, in which case the re-scaled image data can be received by another image coloring processor 158, which can provide false colors to the re-scaled image data 156 according to intensities, to provide artificially colored EL image data 160. However, in other arrangements the calibrated EL image data 128b can be representative of color images, and therefore, the image coloring processor 158 is not used and the image re-scaling processor 154 provides colored EL image data 160a.

An image combining processor 168 can receive the artificially colored FL image data 140 and the artificially colored EL image data 160 (or colored EL image data 160a) and can provide combined image data 170 to a display device, for example, the display device 60 of FIG. 1. Artificially colored FL images and artificially colored (or colored) EL images can be viewed on the display device in real-time, as separate images or as combined images, for example, images that are overplayed.

In some arrangements, the image combining processor 168 can also receive other image data 172 from another imaging system, for example, from a magnetic resonance imaging system, a computer tomography system, an x-ray system, a fluoroscopy system, or a positron emission tomography system. With these arrangements, the artificially colored FL image data 140, the artificially colored EL image data 160 (or colored EL image data 160a), and the other image data 172 can be combined to provide the combined image data 170. With these arrangements, the artificially colored FL images, the artificially colored (or colored) EL images, and other images, which are associated with the other above-described systems, can be viewed on the display device in real-time, as separate images or as combined images, for example, images that are overplayed.

It should be appreciated that FIGS. 3-8 show flowcharts corresponding to the below contemplated technique which would be implemented in an imaging processor 100 (FIG. 2). Rectangular elements (typified by element 354 in FIG. 7), herein denoted "processing blocks," represent computer software instructions or groups of instructions. Diamond shaped elements (typified by element 358 in FIG. 7), herein denoted "decision blocks," represent computer software instructions, or groups of instructions, which affect the execution of the computer software instructions represented by the processing blocks.

Alternatively, the processing and decision blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of blocks described is illustrative only and can be varied without departing from the spirit of the invention. Thus, unless otherwise stated the blocks described below are unordered meaning that, when possible, the steps can be performed in any convenient or desirable order.

Figure 3:
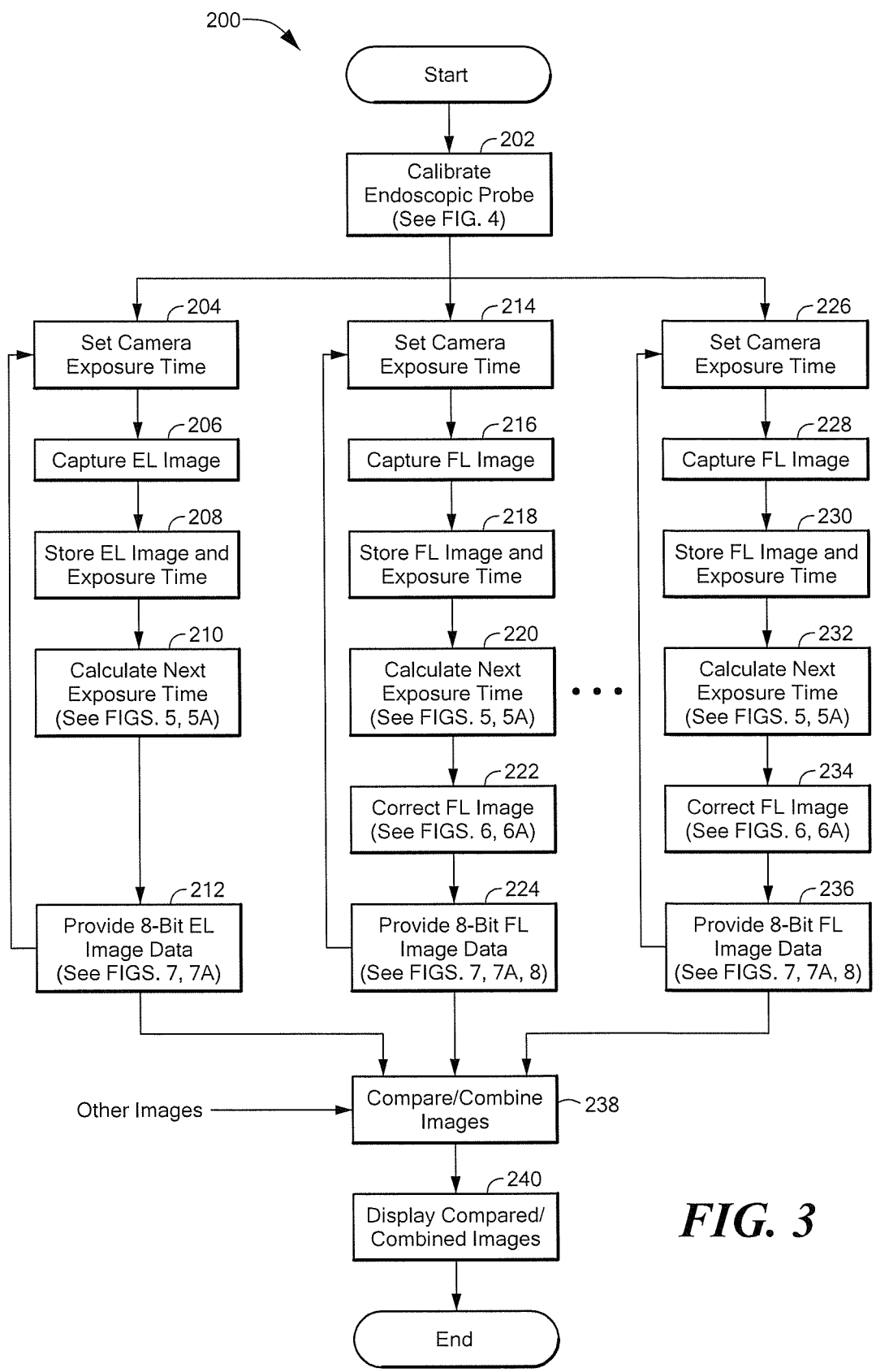
FIG. 3 is flow chart showing an exemplary process that can be used to generate one or more corrected images of fluorescent light.

Referring now to FIG. 3, an exemplary method 200, begins at block 202, where an insertable instrument, for example, an endoscopic instrument, is calibrated. The calibration process is further described below in conjunction with FIG. 4. However, let it suffice here to say that the calibration process of block 202 can identify a region of interest (ROI) in image data, spatially align a plurality of image channels (e.g., excitation light and fluorescent light channels) associated with the image data and with the insertable instrument, and can identify an autofluorescence level associated with fluorescent light channels. Therefore, subsequently captured images can be aligned, cropped to provide only data in the region of interest, and an autofluorescence level can be subtracted to provide a more accurate view of fluorescence activity from fluorochromes.

Blocks 204-212 depict process steps associated with images of excitation light, for example EL images represented by the image data 38 of FIG. 1. Blocks 214-224 depict process steps associated with images of fluorescent light, for example FL images represented by the image data 36 of FIG. 1. Blocks 226-236 depict process steps associated with further images of fluorescent light, for example fluorescent light associated with another fluorochrome that emits fluorescent light at a different wavelength than that of blocks 212-222.

At block 204, an initial exposure time is selected for an excitation light detector (e.g., CCD 34 of FIG. 1). It will be understood that an EL image captured with the initial exposure time may be overexposed, underexposed, or properly exposed. In some embodiments, the initial exposure time is selected as a mid point of a known range of suitable exposure times. However, another initial exposure time can also be used.

At block 206, an excitation light (EL) image is captured, resulting in EL image data, e.g., the image data 38 of FIG. 1.

At block 208, the EL image (i.e., image data) and the exposure time are stored. The storage can include storage to a random access memory (RAM), e.g., the RAM 112 of FIG. 2. In some embodiments, the storage can also include storage to a disk drive or the like, for example, the storage device 116 of FIG. 2, for archiving and later retrieval.

At block 210, a next exposure time is calculated using characteristics of the EL image data captured at block 206. Details of the calculations involved to establish a next exposure time are described below in conjunction with FIGS. 5 and 5A. In general, the EL image data captured at block 206 is examined to identify pixel values that are large or small digital values, and the next exposure time is adjusted accordingly.

At block 212, an EL image (i.e., EL image data) is provided according to the image captured at block 206. The process of block 212 is described more fully below in conjunction with FIGS. 7 and 7A. At block 212, the EL image data can be re-scaled to provide, for example, eight-bit image data. The EL image can also be colored according to a predetermined intensity to color mapping if desired.

The process 200 can return to block 204, where another EL image is captured using the new exposure time calculated at block 210, and the process 200 can concurrently proceed to block 238.

At block 214, an initial exposure time is selected for a fluorescent light detector (e.g., CCD 28 of FIG. 1). It will be understood that an FL image captured with the initial exposure time may be overexposed, underexposed, or properly exposed. In some embodiments, the initial exposure time is selected as a mid point of a known range of suitable exposure times. However, another initial exposure time can also be used. The known range of suitable exposure times for the fluorescent light image will be substantially longer than the known range of suitable exposure times for the excitation light image captured at block 204, since the fluorescent light is generally much less intense than the excitation light.

At block 216, a fluorescent light (FL) image is captured, resulting in FL image data, e.g., the image data 36 of FIG. 1.

At block 218, the FL image (i.e., image data) and the exposure time are stored. The storage can include storage to a random access memory (RAM), e.g., the RAM 112 of FIG. 2. In some embodiments, the storage can also include storage to a disk drive or the like, for example, the storage device 116 of FIG. 2, for archiving and later retrieval.

At block 220, a next exposure time is calculated using characteristics of the FL image data captured at block 216. Details of the calculations involved to establish a next exposure time are described below in conjunction with FIGS. 5 and 5A. In general, the FL image data captured at block 206 is examined to identify pixel values that are large or small digital values, and the next exposure time is adjusted accordingly.

At block 222, the FL image is "corrected." The correction process of block 222 is described more fully below in conjunction with FIGS. 3, 6 and 6A, and also in conjunction with FIGS. 11-11C and 12-12C. However, in general, the correction of block 222 can combine the EL image data captured at block 206 with the FL image data captured at block 216 to provide FL images that are generally invariant with respect to a distance between an insertable instrument and biological tissue being imaged and with respect to an angle of the insertable instrument relative to the biological tissue. The corrected images have an improved exposure consistency from image to image and also across each image, which would otherwise tend to be brighter at the center of an image than at the edges.

The above-described corrected FL images can be used to quantitatively measure signal intensity in a region of interest in any image of a collection of images taken in real time (or in non-real time). Because, as shown below in conjunction with FIGS. 11-11C and 12-12C, the corrected FL images are generally invariant in signal intensity with respect to distance and angle of an insertable instrument relative to a biological tissue, corrected images taken in real time (or in non real time) can be used in combination to provide a continuous dynamic image display in real time that can quantitatively depict image intensity or, in some embodiments, a quantitative concentration of fluorescent probes as the insertable instrument is moved in the body.

At block 224, a corrected FL image (i.e., FL image data) is provided according to the corrected FL image generated at block 222. The process of block 224 is described more fully below in conjunction with FIGS. 7 and 7A. At block 224, the FL image data can be re-scaled if desired to provide, for example, eight-bit image data. The FL image can also be colored in accordance with a predetermined intensity to color mapping, or it can be colored according to concentrations of fluorochrome molecules or autofluorescence generating molecules in the biological tissue. A process resulting in image coloring according to concentrations of fluorochrome molecules or autofluorescence generating molecules is described more fully below in conjunction with FIG. 8.

The process 200 can return to block 214, where another FL image is captured using the new exposure time calculated at block 220, and the process 200 can concurrently proceed to block 238.

Blocks 226-236 describe process blocks that are substantially the same as the process blocks 214-224, but for a different FL image captured in a different FL image channel (not shown) in the light receiver 12 of FIG. 1, for example, at a different fluorescence wavelength associated with a different fluorochrome or a different part of the autofluorescence spectrum. Thus, blocks 226-236 are not further described.

At block 238, the EL and FL images can be combined to provide a combined display at block 240. The combined display can include separate EL and FL images, or combined EL and FL images, for example, images that are overlaid. In some arrangements, as described above in conjunction with FIG. 2, other image data can be received from other types of imaging systems and the other image data can also be combined with the EL and FL images.

Referring now to FIG. 4, a process 250 can be the same as or similar to the process described by block 202 of FIG. 3. At step 252, a known target is imaged and corresponding image data is collected. The image data is collected from a plurality of imaging channels. For example, the image data 36 and 38 of FIG. 1 is collected. The image data includes pixel data corresponding to a full field of view (FOV) of each channel a light receiver (e.g., the light receiver 12 of FIG. 1). However, only a portion of the FOV of each image may be of interest. A portion of the FOV (i.e., a region of interest (ROI)) is selected at lock 254. The ROI corresponds to a portion of the image data of each image collected at block 252.

At block 256, the ROI of the images collected at block 252 are aligned to provide alignment information. The alignment can be done is a variety of ways. In one particular embodiment, the alignment is performed with an affine transformation. In another embodiment, the alignment is performed manually.

The ROI and the alignment information can be used when collecting subsequent images in the process of FIG. 3, resulting in calibrated images that are aligned and which have the same ROI for the different optical channels of the light receiver 12 of FIG. 1. Any number of optical channels can be calibrated in this way.

At block 258, an autofluorescence signal level can be identified in one or more of the fluorescent light optical channels. For example, the known target imaged at block 252 can be a biological tissue having an autofluorescence the same as or similar to that of the biological tissue subsequently imaged. The autofluorescence level can be subtracted from FL images subsequently captured, where the images being captured are images of fluorescent light plus light associated with autofluorescence.

Referring now to FIGS. 5 and 5A, processes 270 and 280 represent alternate processes that can be used to calculate a next exposure time in the process blocks 210, 220, 232 of FIG. 3.

Referring first to FIG. 5, the process 270 begins at block 272 where a largest pixel intensity value, i.e., a pixel value representative of a highest light intensity, is identified in a region of interest of an image captured, for example, at block 206 of FIG. 3. At block 274, the largest pixel value is combined with a previous exposure time to provide a next exposure time.

The new exposure time for the next image can be calculated in the following way. The exposure time is adjusted such that the image intensity approaches a previously defined set point, S. Equation (1) describes the algorithm by which the new exposure time can be determined:

$$\text{new} = \left(1 - \frac{P-S}{S}\right) * \text{old} \tag{1}$$

where new is the next exposure time, old is the previous exposure time, P is a measure of the image intensity of a captured image, and S is the set point. The value for P can be a value of the largest pixel value identified at block 272, or a predetermined fraction of the largest pixel value.

Limits can be established to ensure that the exposure time never falls below a minimum, for example, 100 μs, or exceeds a maximum, for example, 290 ms. Moreover, the new exposure time can be constrained to be within 30% of the previous exposure time to prevent excessive fluctuations. However, this constraint is rarely required when using relatively fast cameras, as most exposure time adjustments, except in the most extreme (and artificially created) cases, have been found to be within 20% of the previous exposure time, even with very rapid movement of an insertable instrument.

Referring now to FIG. 5A, and process 280 begins at block 282, where a histogram of pixel intensity values in an ROI of a captured image is generated. At block 282, a percentage-of-histogram-area value is selected. For example, the percentage-of-histogram-area value can be about ninety-five percent. A range of useful percentage-of-histogram-area values is about twenty-five percent to one hundred percent.

At block 286 an actual pixel intensity value is identified according to the percentage-of-histogram-area value selected at block 284. For example, if 95% of the pixel intensity values are below an eight-bit digital value of 227, then the value 227 is identified at block 286.

At block 288, the identified pixel value is combined with a previous exposure time to provide a next exposure time. The combining can be performed in much the same way as described above in conjunction with Equation (1), however, the value P here can be the identified pixel value according to block 286.

Figure 6:
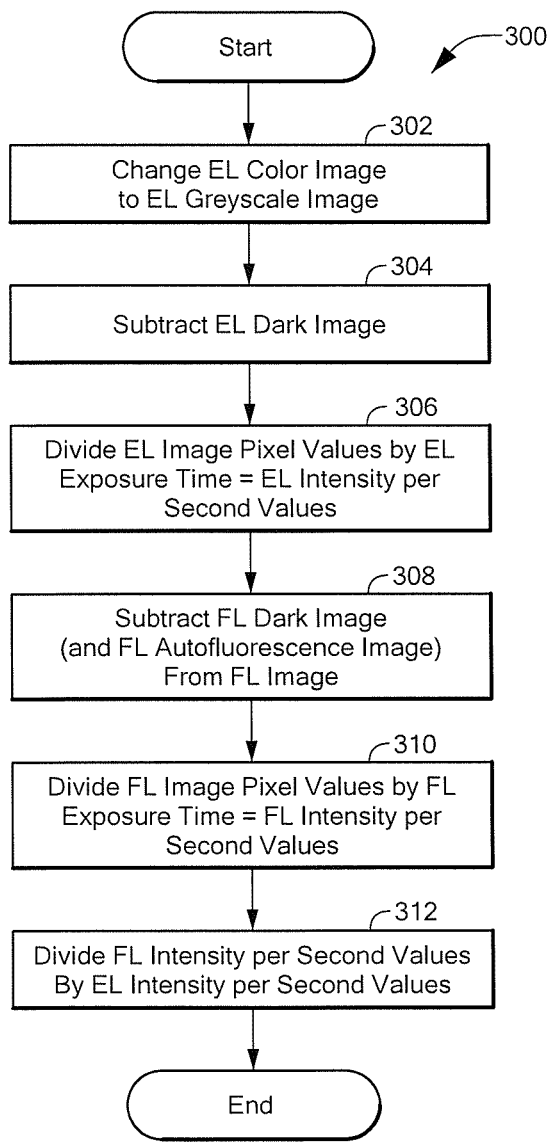
FIG. 6 is a flow chart showing an image correction process, which is indicative of further details of the process of FIG. 3.

Referring now to FIG. 6, an image correction process 300 can be the same as or similar to the process of blocks 222, 234 of FIG. 3. The process 300 is used to "correct" a fluorescence image.

In general, as described above, intravital access achieved with catheter or endoscope based systems having an insertable instrument tends to reduce dynamic range compared with fixed systems in which the camera to the biological tissue distance is constant. Systems having an insertable instrument tend to produce images with excessive brightness when the insertable instrument is closer to a biological tissue being imaged and excessive dimness when the insertable instrument is farther from the biological tissue. Image data can vary in intensity over orders of magnitude even for fixed concentrations of fluorochrome, given the continually changing distance from the insertable instrument to the biological tissue. Real-time adjustment of exposure on a frame by frame basis, as provided, for example, by blocks 204-212, 214-224, and 226-236 of FIG. 3, tends to equalize the intensity of images on an image by image basis, which would otherwise vary greatly. However, adjustment of exposure time on a frame by frame basis also tends to result in images that cannot be readily compared or combined, since the images can be the result of greatly differing exposure times. Therefore, the process 300, can provide images not only improved in intensity matching, but also can provide images that can be compared and/or combined.

The process 300 begins at block 302, where, if an excitation light image captured at block 206 of FIG. 3 is a color image, the color image is converted to a gray scale image. As is known, CCD color cameras, both sophisticated and consumer digital cameras, acquire images in grayscale. The grayscale images can be colorized by the camera using a so-called Bayer algorithm. A variety of techniques can be employed to convert the color images to grayscale images. The techniques include, but are not limited to averaging red, green, and blue (RGB) values at each pixel to calculate a grayscale pixel intensity used in a grayscale image. In general, it will be apparent that RGB pixel values can be combined in one of a variety of ways to provide grayscale values.

At block 304, a dark image (i.e., a background noise image collected in the absence of excitation and fluorescent light) can optionally be subtracted from the captured EL image.

At block 306, the individual pixel intensity values in the EL image are divided by an exposure time (see e.g., signals 126, 111b of FIG. 1) at which the EL image was captured, to provide so-called EL intensity-per-second values associated with the EL image. However, in other embodiments, the individual pixel intensity values in the EL image are combined in some other way with the associated exposure time.

At block 308 a dark image (i.e., a background noise image collected in the absence of excitation and fluorescent light) can optionally be subtracted from a captured FL image, for example, an FL image captured at block 216 of FIG. 3. Optionally, an autofluorescence signal, for example the autofluorescence signal identified at block 258 of FIG. 4 during a calibration process, can also be subtract from the captured FL image.

At block 310, the individual pixel intensity values in the FL image are divided by an exposure time (see e.g., signals 128, 149b of FIG. 1) at which the FL image was captured, to provide FL intensity-per-second values associated with the FL image. However, in other embodiments, the individual pixel intensity values in the FL image are combined in some other way with the associated exposure time.

It will be understood that by dividing the pixel intensity values of an image (minus dark image) by a respective exposure time, on an image by image basis, the resulting image data is exposure time-independent, in so-called intensity-per-second units. Therefore, the intensity-per-second image data can be used to compare and/or combine pixel intensity values (i.e., images) from different images.

Also, use of intensity-per-second values results in a greatly increased dynamic range. For example, while the raw image intensity values of a twelve-bit system range from 0 to $2^{12}$, the intensity-per-second image data can take any value from 0 to $2^{12}$ divided by the range of possible exposure times (e.g., approximately 100 μs to 290 ms, or $\sim 2^{18}$). This results in $\sim 2^{30}$ possible values, resulting in an effective 30-bit dynamic range. This precision is much greater than most clinical imaging systems and can be applied to each of multiple channels independently.

At block 312, the FL intensity-per-second values are combined with, e.g., divided by, the EL intensity-per-second values to provide corrected FL image values, or a corrected image. While the combination of the FL and EL intensity-per-second values is described to be a division, in other embodiments, the FL and EL intensity-per-second values can be combined in a different way.

It will be understood in conjunction with FIGS. 11-11C and 12-12C that the above-described correction process results in a corrected image that has an intensity that is generally invariant with respect to a distance of an insertable instrument from a biological tissue being imaged and with respect to an angle of the insertable instrument relative to the biological tissue. In essence, as further described below, because both the FL and EL image per second values have similar distance and angle dependence, a ratio of the FL and EL image per second values (i.e., a corrected FL image, see e.g., blocks 222 and 234 of FIG. 3) provides an image that is generally invariant with respect to distance and angle of the insertable instrument relative to a biological tissue. Therefore, successive corrected FL images taken in real time can provide a real-time display of FL image intensity, and in some embodiments further described below, of quantitative fluorescent probe concentration.

Figure 6A:
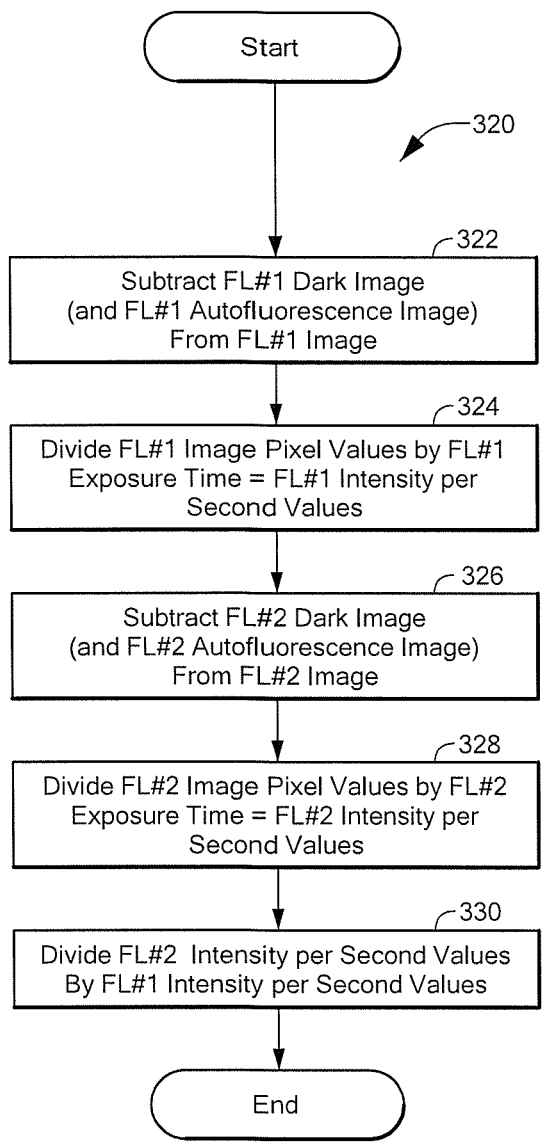
FIG. 6A is a flow chart showing another image correction processes, which is indicative of further details of the process of FIG. 3 as an alternative to the process of FIG. 6.

Referring now to FIG. 6A, another image correction process 320 can be the same as or similar to the process of blocks 222, 234 of FIG. 3. The process 320 is particularly useful when the insertable instrument is in a diffuse medium, for example, in a blood vessel filled with blood. The utility of the process 320 will become more evident in discussion in conjunction with FIGS. 13-13B.

The process 320 involves two fluorescence imaging channels, unlike FIG. 1, which shows only one fluorescence imaging channel, which results in the image data 36. However, as described above, a light receiver similar to the light receiver 12 of FIG. 1 can have more than one fluorescence imaging channel and can provide more than one FL image data. In nomenclature used below, a first fluorescence image and image data associated therewith are referred to a FL#1 and a second fluorescence image and image data associated therewith are referred to a FL#2.

At block 322, a dark image (i.e., a background noise image collected in the absence of excitation and fluorescent light) can optionally be subtracted from a first captured FL image, FL#1, for example, an FL image captured at block 216 of FIG. 3. Optionally, an autofluorescence signal, for example the autofluorescence signal identified at block 258 of FIG. 4 during a calibration process, can also be subtract from the captured FL#1 image.

At block 324, the individual pixel intensity values in the FL#1 image are divided by an exposure time (see e.g., signals 128, 149b of FIG. 1) at which the FL#1 image was captured, to provide FL#1 intensity-per-second values associated with the FL#1 image. However, in other embodiments, the individual pixel intensity values in the FL#1 image are combined in some other way with the associated exposure time.

At block 326, a dark image (i.e., a background noise image collected in the absence of excitation and fluorescent light) can optionally be subtracted from a second captured FL image, FL#2, for example, an FL image captured at block 228 of FIG. 3. Optionally, an autofluorescence signal, for example the autofluorescence signal identified at block 258 of FIG. 4 during a calibration process, can also be subtract from the captured FL#2 image.

At block 328, the individual pixel intensity values in the FL#2 image are divided by an exposure time (see e.g., signals 128, 149b of FIG. 1) at which the FL#2 image was captured, to provide FL#2 intensity-per-second values associated with the FL#2 image. However, in other embodiments, the individual pixel intensity values in the FL#2 image are combined in some other way with the associated exposure time.

At block 330, the FL#2 intensity-per-second values are combined with, e.g., divided by, the FL#1 intensity-per-second values to provide corrected FL image values, or a corrected FL image. It will be understood from discussion in conjunction with FIGS. 11-11C and 12-12C that the above-described correction process results in a corrected image that has an intensity that is generally invariant with respect to a distance of an insertable instrument from a biological tissue being imaged and with respect to an angle of the insertable instrument relative to the biological tissue. It will also be apparent from discussion in conjunction with FIGS. 13-13B that this process, using two fluorescent channels, can result in an ability to generate quality images even in the presence of a optically absorptive medium, for example, blood. In essence, as further described below, because both the FL#2 and FL#1 image per second values have similar distance and angle dependence, a ratio of the FL#2 and FL#1 image per second values (i.e., a corrected FL image, see e.g., blocks 222 and 234 of FIG. 3) provides an image that is generally invariant with respect to distance and angle of the insertable instrument relative to a biological tissue through a volume of optically absorptive medium.

Referring now to FIGS. 7 and 7A, processes 350 and 370 represent alternate processes that can be used to provide eight-bit image data in the process blocks 212, 224, 236 of FIG. 3.

Referring first to FIG. 7, the process 270 begins at block 352 where an eight-bit image can be generated. At block 354, a largest pixel value is identified in a region of interest (ROI) of a captured image, for example, an image captured at blocks 206, 216, or 228 of FIG. 3. The captured image data can have any number of bits per pixel, for example, twelve bits per pixel.

At block 356, the captured image data can be converted to a different number of bits per pixel according to the largest pixel value identified at block 354.

The image can be scaled, for example, from twelve-bit to eight-bit image data for display on a computer monitor. Equation (2) describes a relationship that can be used to $$pixel' = pixel * \frac{255}{P} \quad (2)$$

where pixel' is an eight-bit rescaled image data value of an original twelve-bit image data value, pixel, and P is a twelve-bit pixel value according to a maximum pixel value identified at block 354.

At block 358, if the captured image is an excitation light (EL) image, which may be a colored image, the process ends. However, if the captured image in not an EL image, but is instead a fluorescent light (FL) image, which is not colored, then the process continues to block 360. At block 360 the non-colored FL image can be colored. In some embodiments, the coloring can be arbitrary, wherein arbitrary colors are assigned to respective ranges of pixel intensity values. In other embodiments, the colors applied at block 360 are applied in accordance with a mapping of pixel intensity values to colors by a process described below in conjunction within FIG. 8.

In embodiments for which the captured EL image is not colored, then the decision block 358 is ignored and the process proceeds to block 360, where the EL image is colored.

Referring now to FIG. 7A, the process 370 begins at block 372 where an eight-bit image can be generated. At block 374, a histogram of pixel intensity values is generated within a region of interest (ROI) of a captured image, for example, an image captured at blocks 206, 216, or 228 of FIG. 3. The captured image data can have any number of bits per pixel, for example, twelve bits per pixel.

At block 374, a percentage-of-histogram-area value is selected. For example, the percentage-of-histogram-area value can be about ninety-five percent. A range of useful percentage-of-histogram-area values is about twenty-five percent to one hundred percent.

At block 378 an actual pixel intensity value is identified according to the percentage-of-histogram-area value selected at block 376. For example, if 95% of the pixel intensity values are below a twelve-bit digital value of 4003, then the value 4003 is identified at block 378.

At block 380, the captured image data can be converted to a different number of bits per pixel according to the pixel value identified at block 378. The conversion can use a relationship a described above in equation (2), however, the value P can be the pixel intensity value identified at block 378.

At block 382, if the captured image is an excitation light (EL) image, which may be a colored image, the process ends. However, if the captured image in not an EL image, but is instead a fluorescent light (FL) image, which is not colored, then the process continues to block 384. At block 384 the non-colored FL image can be colored. In some embodiments, the coloring can be generated according to a predetermined intensity to color mapping, wherein predetermined colors are assigned to respective ranges of pixel intensity values. In other embodiments, the colors applied at block 384 are applied in accordance with a mapping of pixel intensity values to colors by a process represented in FIG. 8.

In embodiments for which the captured EL image is not colored, then the decision block 382 is ignored and the process proceeds to block 384, where the EL image is colored.

Figure 8:
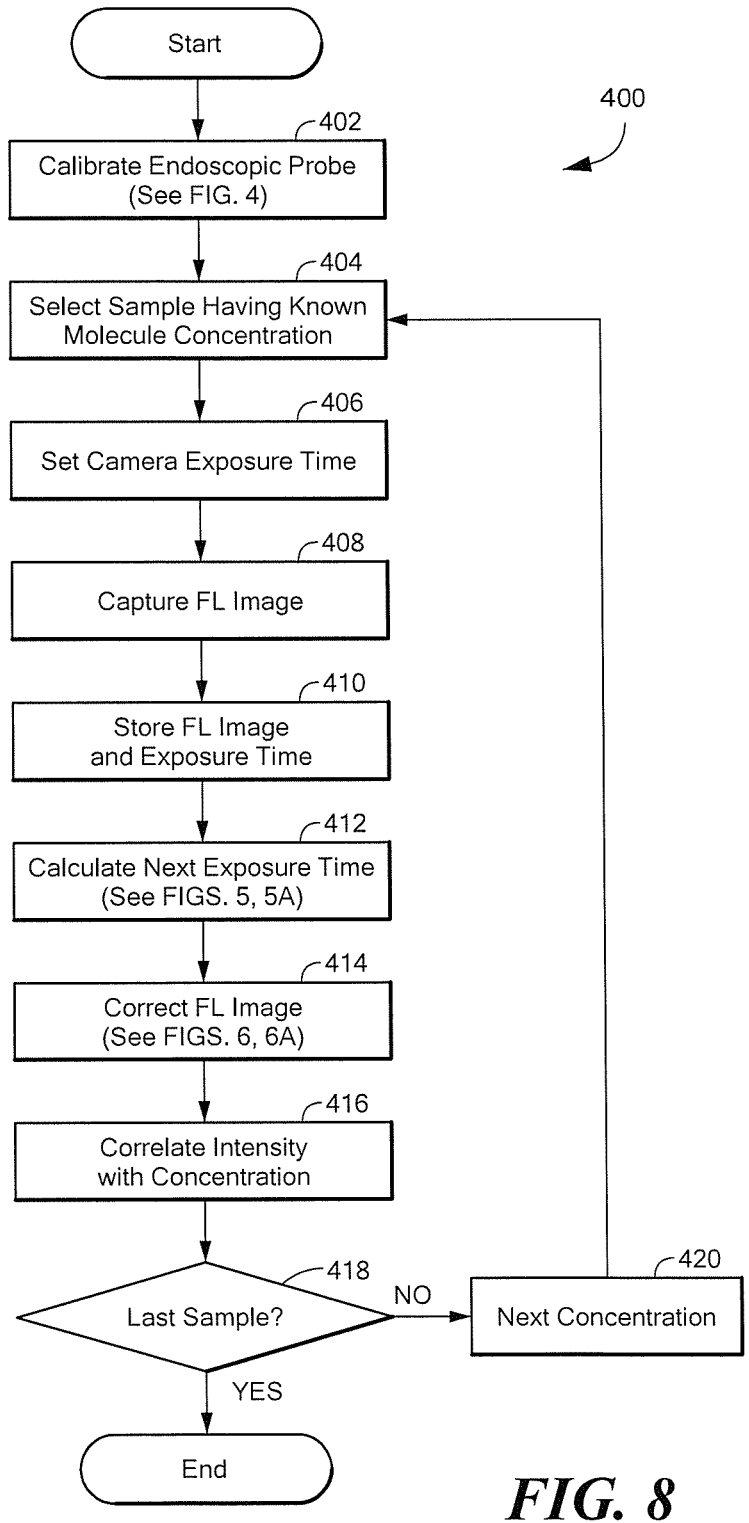
FIG. 8 is a flow chart showing an intensity-to-molecule-concentration mapping process, which is indicative of further details of the process of FIG. 3.

Referring now to FIG. 8, a process 400 for generating a map of pixel intensity values to molecule concentrations begins at block 402. Blocks 402 and 406-414 can be the same as or similar to blocks 202 and 214-222 of FIG. 3, and therefore, are not described again.

At block 404, a test sample having a known concentration of fluorescent generating molecules, for example, a known concentration of fluorochrome molecules is selected. The process of blocks 406-414 result in corrected FL image data representing a corrected FL image. As described above, the corrected FL image has a variety of processing applied to an uncorrected FL image. For example, the intensity of the corrected FL image is controlled by way of block 412, and the FL image is combined with an EL image at block 414 as described above in conjunction with block 222 of FIG. 3 and with the processes 300 and 320 of FIGS. 6 and 6A. Furthermore, the calibration information of block 402 results in the correct image being formed in a region of interest and being aligned with other images.

At block 416, image pixel intensity values are identified and correlated, i.e., mapped, with respect to the concentration of molecules in the sample selected at block 404.

At block 418, if the sample of block 404 is the last sample, the process ends. If, however, there is a next sample (i.e., another molecule concentration to be mapped), the next concentration is selected at block 420 and the process 400 returns to block 404 where a sample having the known next molecule concentration is selected.

Figure 9:
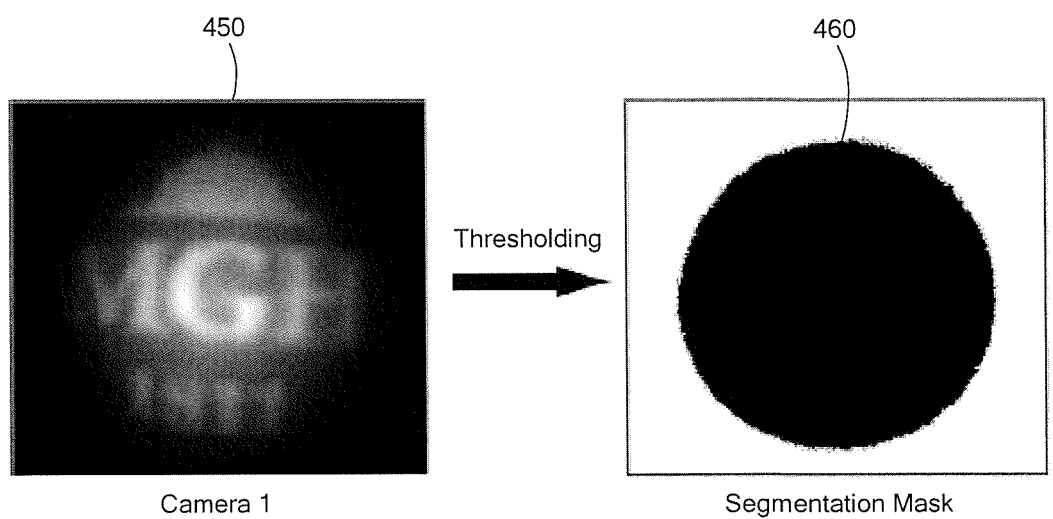
FIG. 9 is an exemplary image generated by the system of FIG. 1.

Referring now to FIGS. 9 and 9A, images 450 and 460 are representative of the process by which a field of view (FOV) is implemented as described above in conjunction with in block 254 of FIG. 4. The image 450 can be seen to be visible only in a central portion of a viewable area. A mask 460 can be identified in a variety of ways. For example, the mask 460 can be comprised of first values (represented by black) in a continuous circular region corresponding to pixel values in the image 450 that are above a predetermined value (i.e., visible). The mask can be comprised of second value everywhere else. The mask can be stored and can be applied to all subsequently captured images, for example, images captured at blocks 206, 216 and 228 of FIG. 3.

Figure 10:
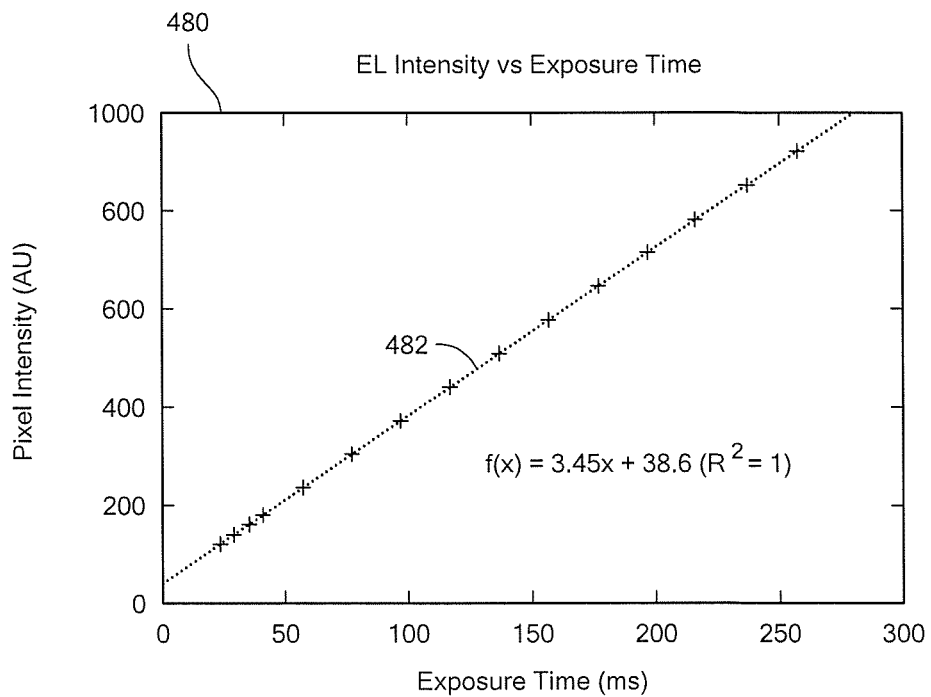
FIG. 10 is a graph showing exposure times versus image pixel intensities for an image of excitation light.

Referring now to FIG. 10, a graph 480 has a horizontal scale in units of exposure time in milliseconds and a vertical axis in units of pixel intensity values in arbitrary units. A curve 482 is representative of a measure relationship between exposure time and pixel intensity values (average of pixel intensity values within the ROI) for an excitation light image.

It will be recognized that the relationship between pixel intensity values and exposure times is relatively linear. It will also be recognized that the exposure times can vary, depending upon the illumination intensity from relatively short to relatively long. Often, in biological systems, the reflected EL exposure times are much shorter than the collected fluorescence light exposure times. However, to collect FL images, a higher intensity excitation light source can be used, resulting in shorter exposure times, as is apparent in FIG. 10A.

Figure 10A:
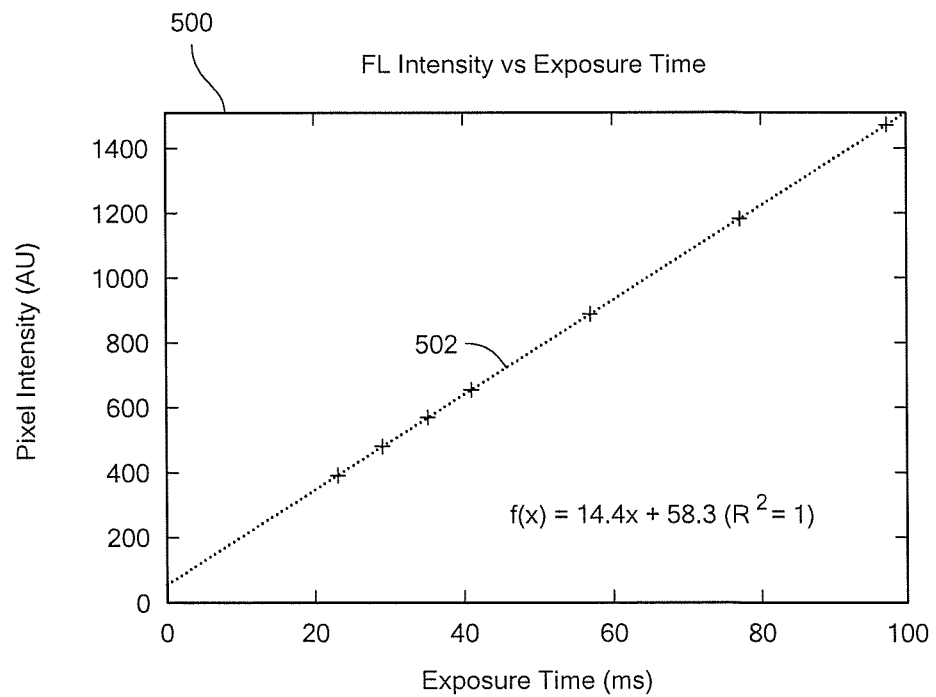
FIG. 10A is a graph showing exposure times versus image pixel intensities for an image of fluorescent light.

Referring now to FIG. 10A, a graph 500 has a horizontal scale in units of exposure time in milliseconds and a vertical axis in units of pixel intensity values in arbitrary units. A curve 502 is representative of a measure relationship between exposure time and pixel intensity values (average of pixel intensity values within the ROI) for a fluorescent light image.

It will be recognized that the relationship between pixel intensity values and exposure times is relatively linear.

Figure 11:
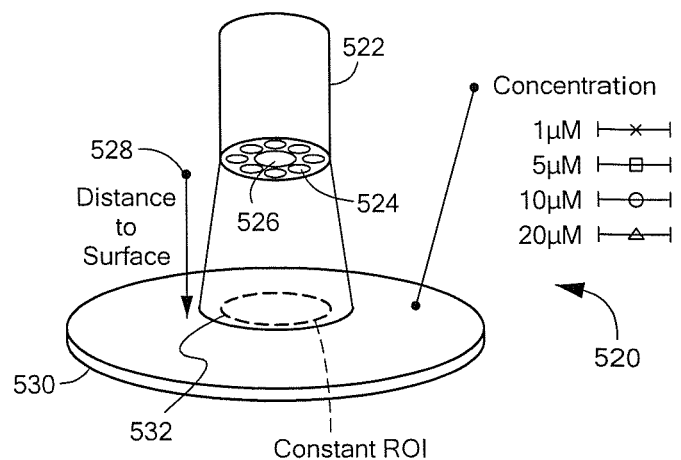
FIG. 11 is pictorial showing an insertable instrument in distance relation to a surface.
Figure 11A:
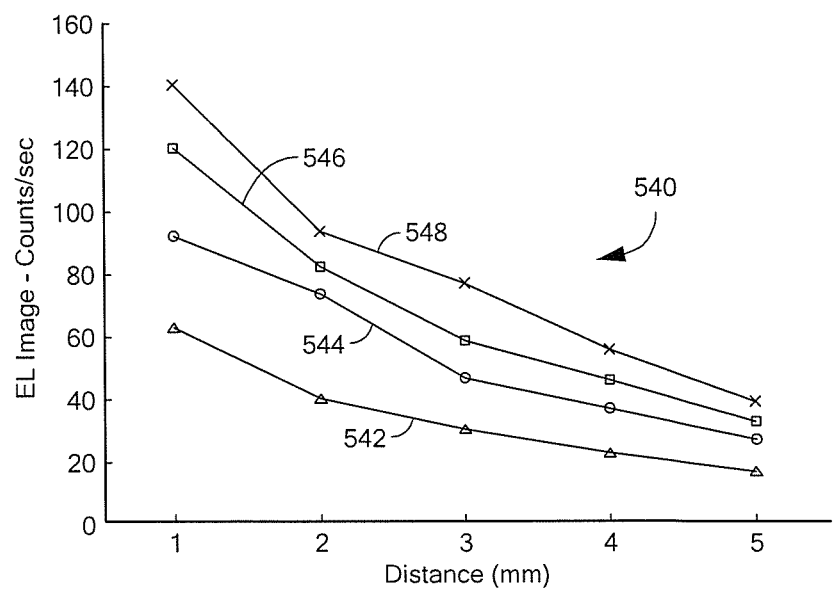
FIG. 11A is a graph showing a relation between insertable instrument distance and pixel intensity for an image of excitation light.
Figure 11B:
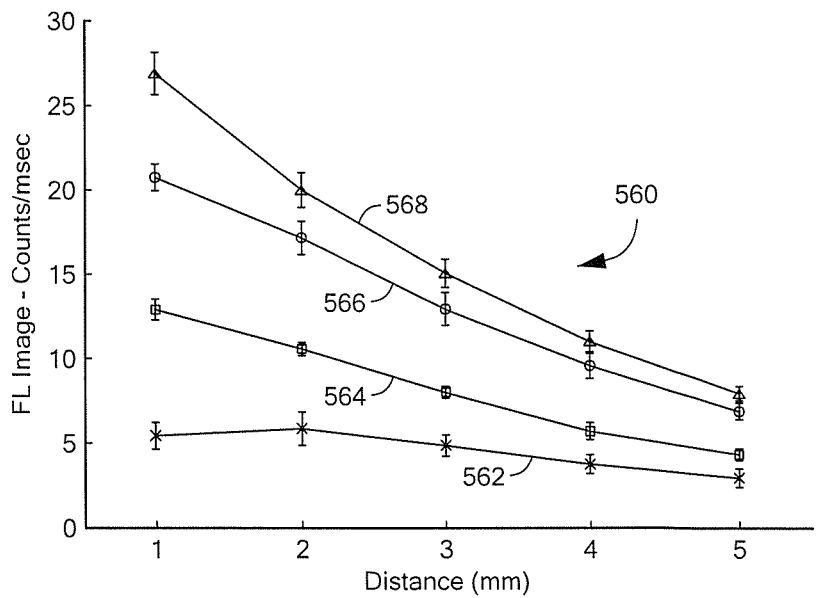
FIG. 11B is a graph showing a relation between insertable instrument distance and pixel intensity for an image of fluorescent light.
Figure 11C:
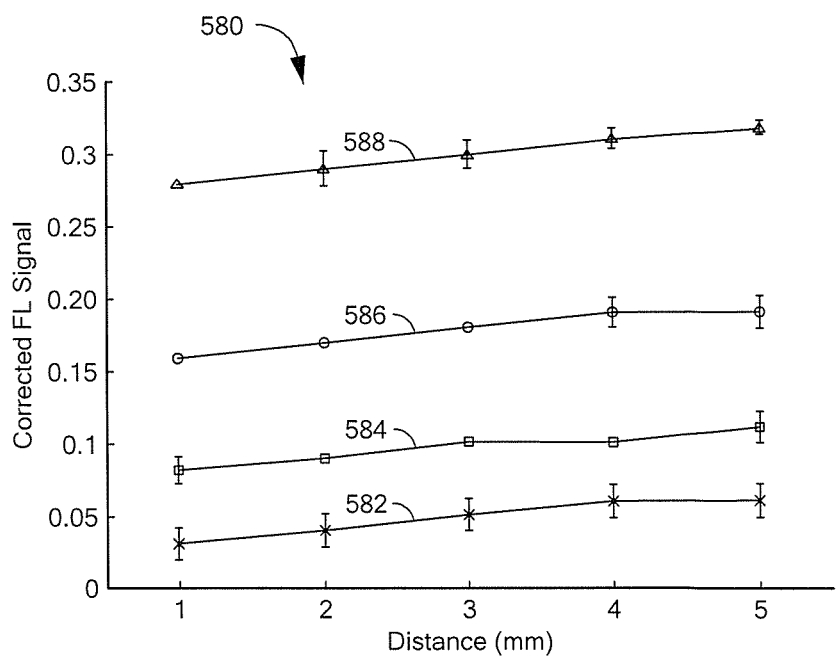
FIG. 11C is a graph showing a relation between insertable instrument distance and pixel intensity for a corrected image of fluorescent light in accordance with techniques described herein.

FIGS. 11-11C show a process of FL image correction described above in conjunction with FIG. 6 and the effect of distance of the insertable instrument on resulting images.

Referring first to FIG. 11, a pictorial 520 shows an insertable instrument 522 having a plurality of optical fibers, of which an optical fiber 524 is but one example, arranged about the outer portion of a fiber optic cable or fiber optic bundle. The plurality of optical fibers is adapted for transmission of excitation light. Another optical fiber 526 at the center of the insertable instrument 522 is adapted for reception of excitation and fluorescent light.

A sample 530, which has a region of interest (ROI) 530, identified by the process shown in FIGS. 9 and 9A, has a uniform concentration of fluorochromes. In experimental use, the insertable instrument 522 can be positioned at a variety of distances 528 relative to the ROI 532. Fluorochrome concentrations of twenty, ten, five, and one micromolar are used for measurements described below.

The insertable instrument can be coupled to a light transmitter and a light receiver, for example the light transmitter 42 of FIG. 1 and the light receiver 12 of FIG. 1. As described above, the light receiver 12 can provide EL image data 38 representative of an EL image of the ROI 532, and FL image data 36 representative of an FL image of the ROI 532.

Referring now to FIG. 11A, a graph 540 includes a horizontal axis having units of distance (528, FIG. 11) in millimeters. The graph 540 also includes a vertical axis having units of pixels intensity in units of counts per second, which is equivalent to the intensity-per-second value described above in conjunction with FIG. 6. It should be understood from FIG. 6 that in order to achieve the intensity-per-second values, image data values are divided or otherwise combined with an exposure time value associated with the image.

A first curve 542 shows measured EL image data values (i.e., pixel intensity values) representative of an image of the ROI 532 of FIG. 11, namely an average pixel intensity-per-second value in the ROI 532 when the insertable instrument 522 of FIG. 11 is at distances of one, two, three, four, and five millimeters from the ROI 532 for a fluorochrome concentration of one micromolar. A second curve 544 shows measured EL image data values representative of an image of the ROI 532 of FIG. 11, namely an average pixel intensity-per-second value in the ROI 532 when the insertable instrument 522 of FIG. 11 is at distances of one, two, three, four, and five millimeters from the ROI 532 for a fluorochrome concentration of five micromolar. A third curve 546 shows measured EL image data values representative of an image of the ROI 532 of FIG. 11, namely a an average pixel intensity-per-second value in the ROI 532 when the insertable instrument 522 of FIG. 11 is at distances of one, two, three, four, and five millimeters from the ROI 532 for a fluorochrome concentration of ten micromolar. A fourth curve 548 shows measured EL image data values representative of an image of the ROI 532 of FIG. 11, namely an average pixel intensity-per-second value in the ROI 532 when the insertable instrument 522 of FIG. 11 is at distances of one, two, three, four, and five millimeters from the ROI 532 for a fluorochrome concentration of twenty micromolar.

It can be seen that all of the curves 542-548 have a slope indicative of a decreasing EL image intensity as the distance between the insertable instrument 522 and the ROI 532 increases, indicative of dispersion of light proportional to distance squared. This effect, without further correction, can result in a highly variable intensity of EL images for an insertable instrument used in prior art imaging systems as the insertable instrument is moved about in the body.

Referring now to FIG. 11B, a graph 560 includes a horizontal axis having units of distance (528, FIG. 11) in millimeters. The graph 560 also includes a vertical axis having units of pixels intensity in units of counts per millisecond, which is similar to the intensity-per-second value described above in conjunction with FIG. 6.

A first curve 562 shows measured FL image data values representative of an image of the ROI 532 of FIG. 11, namely an average pixel intensity-per-millisecond value in the ROI 532 when the insertable instrument 522 of FIG. 11 is at distances of one, two, three, four, and five millimeters from the ROI 532 for a fluorochrome concentration of one micromolar. A second curve 564 shows measured FL image data values representative of an image of the ROI 532 of FIG. 11, namely a average pixel intensity-per-millisecond value in the ROI 532 when the insertable instrument 522 of FIG. 11 is at distances of one, two, three, four, and five millimeters from the ROI 532 for a fluorochrome concentration of five micromolar. A third curve 566 shows measured FL image data values representative of an image of the ROI 532 of FIG. 11, namely an average pixel intensity-per-millisecond value in the ROI 532 when the insertable instrument 522 of FIG. 11 is at distances of one, two, three, four, and five millimeters from the ROI 532 for a fluorochrome concentration of ten micromolar. A fourth curve 568 shows measured FL image data values representative of an image of the ROI 532 of FIG. 11, namely an average pixel intensity-per-millisecond value in the ROI 532 when the insertable instrument 522 of FIG. 11 is at distances of one, two, three, four, and five millimeters from the ROI 532 for a fluorochrome concentration of twenty micromolar.

It can be seen that all of the curves 562-568 have a slope indicative of a decreasing FL image intensity as the distance between the insertable instrument 522 and the ROI 532 increases, indicative of dispersion of light proportional to distance squared. This effect, without further correction, can result in a highly variable intensity of the FL images when the insertable instrument is moved about in the body.

Referring now to FIG. 11C, a graph 580 includes a horizontal axis having units of distance (528, FIG. 11) in millimeters. The graph 540 also includes a vertical axis having units of pixels intensity in non-dimensional units.

A first curve 582 is generated by dividing the curve 562 of FIG. 11B (i.e., the FL image) by the curve 542 of FIG. 11A (i.e., the EL image). Similarly, a second curve 584 is generated by dividing the curve 564 of FIG. 11B by the curve 544 of FIG. 11A. A third curve 586 is generated by dividing the curve 566 of FIG. 11B by the curve 546 of FIG. 11A. A fourth curve 588 is generated by dividing the curve 568 of FIG. 11B by the curve 548 of FIG. 11A.

The first curve 582 shows corrected FL image data values representative of a maximum pixel intensity in the ROI 532 FIG. 1, when the insertable instrument 522 of FIG. 11 is at distances of one, two, three, four, and five millimeters from the ROI 532 for a fluorochrome concentration of one micromolar. The second curve 584 shows corrected FL image data values representative of a maximum pixel intensity in the ROI 532 FIG. 1, when the insertable instrument 522 of FIG. 11 is at distances of one, two, three, four, and five millimeters from the ROI 532 for a fluorochrome concentration of five micromolar. The third curve 586 shows corrected FL image data values representative of a maximum pixel intensity in the ROI 532 FIG. 1, when the insertable instrument 522 of FIG. 11 is at distances of one, two, three, four, and five millimeters from the ROI 532 for a fluorochrome concentration of ten micromolar. The fourth curve 588 shows corrected FL image data values representative of a maximum pixel intensity in the ROI 532 FIG. 1, when the insertable instrument 522 of FIG. 11 is at distances of one, two, three, four, and five millimeters from the ROI 532 for a fluorochrome concentration of twenty micromolar.

It can be seen that all of the curves 582-588 are more nearly flat than the uncorrected curves 544-548 of FIG. 11A. The curves 882-588 are indicative of corrected images according the above-described technique that have substantially the same intensity irrespective of distance (528, FIG. 11) from the insertable instrument 522 to the ROI 532. It should, however be recognized from the differences between the curves 582-588 that the pixel intensities in the corrected FL images remain indicative of fluorochrome concentrations. Thus, the correction algorithm is able to separate curves corresponding to different fluorochrome concentrations into discrete bands, while the uncorrected curves (FIGS. 11A and 11B) quickly blend into one another.

Figure 12A:
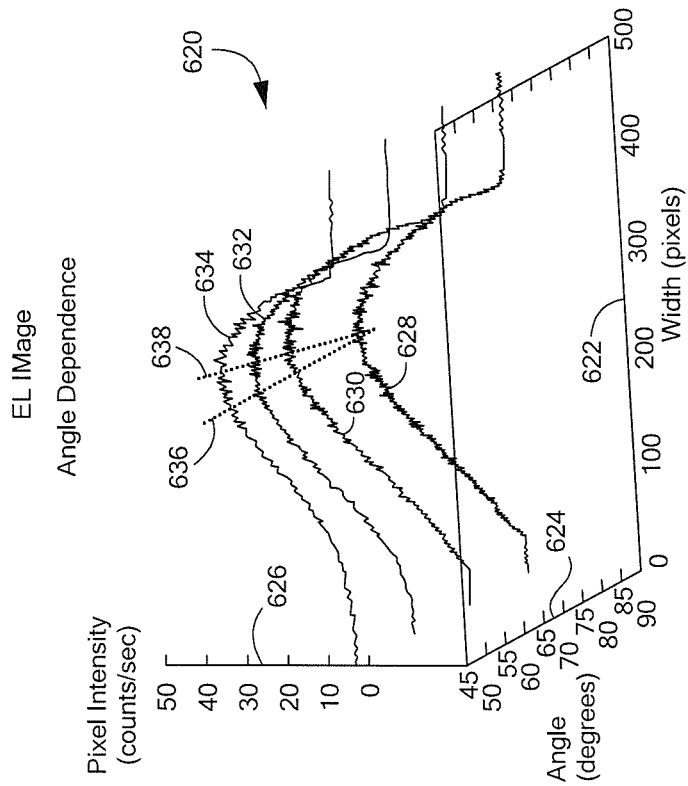
FIG. 12A is a graph showing a relation between insertable instrument angle, pixel intensity, and position within an image for an image of excitation light.
Figure 12:
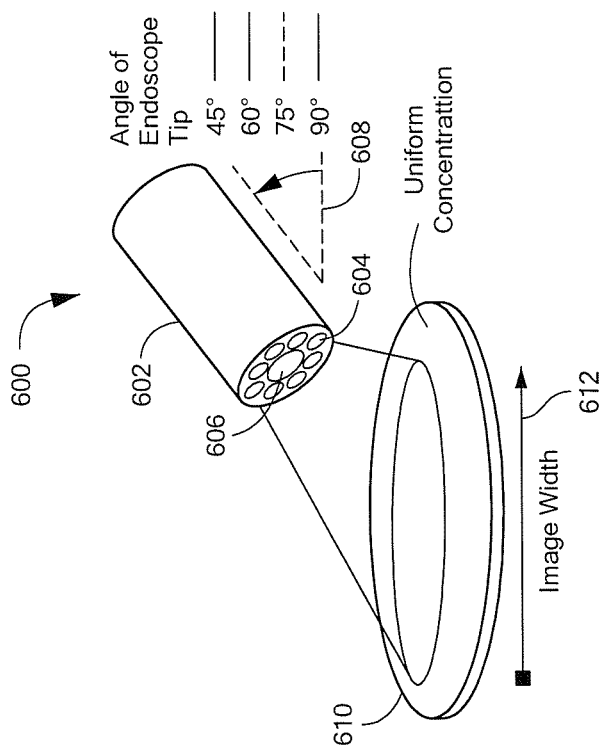
FIG. 12 is pictorial showing an insertable instrument in angle relation to a surface.
Figures 12B, 12C:
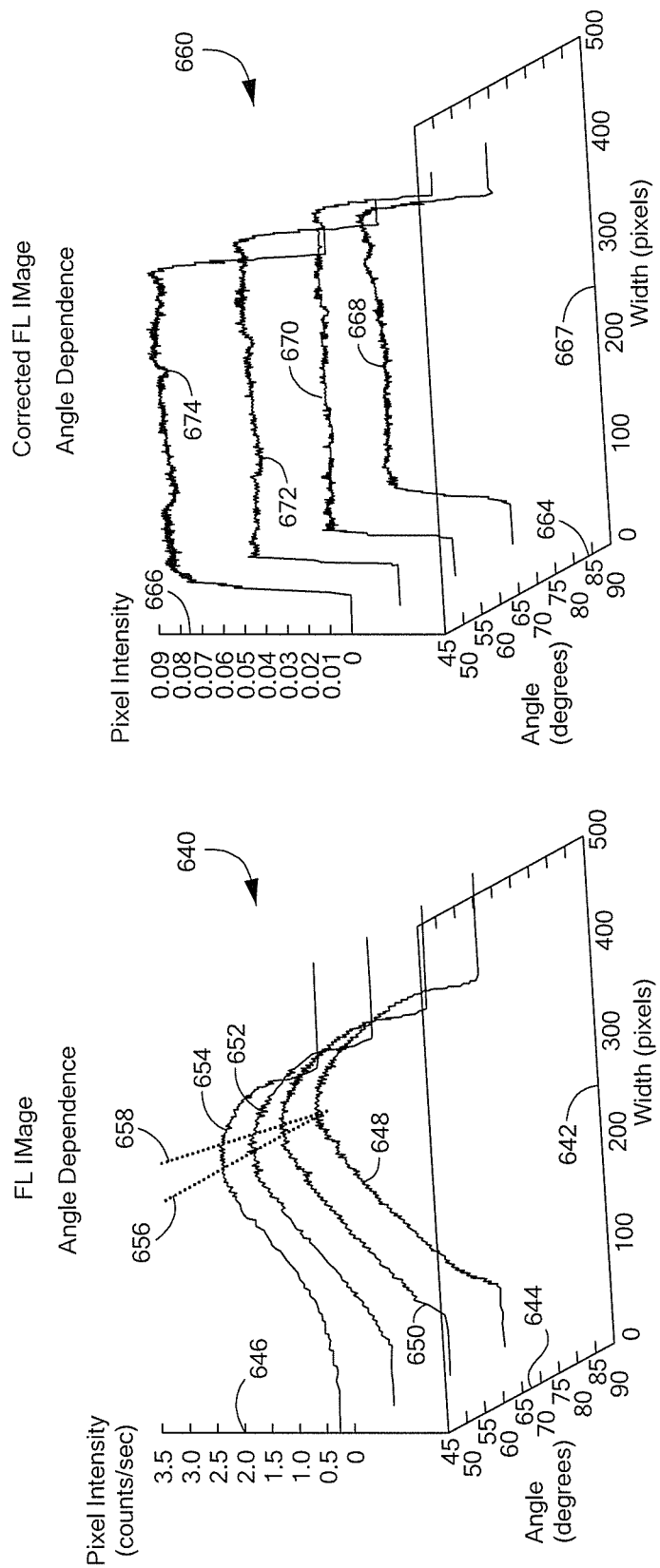
FIG. 12B is a graph showing a relation between insertable instrument angle, pixel intensity, and position within an image for an image of fluorescent light.
FIG. 12C is a graph showing a relation between insertable instrument angle, pixel intensity, and position within an image for a corrected image of fluorescent light in accordance with techniques described herein.

FIGS. 12-12C show graphically, the process of FL image correction described above in conjunction with FIG. 6 and the effect of angle of the insertable instrument on resulting images.

Referring first to FIG. 12, a pictorial 600 shows an insertable instrument 602 having a plurality of optical fibers, of which an optical fiber 604 is but one example, arranged about the outer portion of a fiber optic cable or fiber optic bundle. The plurality of optical fibers is adapted for transmission of excitation light. Another optical fiber 606 at the center of the insertable instrument 602 is adapted for reception of light.

A field of view (FOV) 610 includes a uniform concentration of fluorochromes and has an image width 612. In experimental use, the insertable instrument 602 can be positioned at a variety of angles 608 relative to the FOV 610, here, angles of forty, sixty, seventy-five, and ninety degrees.

The insertable instrument can be coupled to a light transmitter and a light receiver, for example the light transmitter 42 of FIG. 1 and the light receiver 12 of FIG. 1. As described above, the light receiver 12 can provide image data 38 representative of an EL image of the FOV 610, and image data 36 representative of an FL image of the FOV 610.

Referring now to FIG. 12A, a three dimensional graph 620 includes a first axis 622 having units of image width in units of pixels associated with a charge coupled device, for example, the charge coupled device 34 of FIG. 1, which is used to generate EL image data 38 representative of an image of excitation light. The graph 620 also includes a second axis 624 having units of angle in degrees, wherein the angle corresponds to the angle 608 of FIG. 12. The graph 620 also includes a third axis 626 having units of pixel intensity in units of counts per second, which is equivalent to the above described intensity-per-second value described above in conjunction with FIG. 6. It should be understood from FIG. 6 that in order to achieve the intensity-per-second values, image data values are divided or otherwise combined with an exposure time value associated with the image.

A first curve 628 shows measured EL image data values representative of an image along an axis on the FOV 610 of FIG. 12, when the insertable instrument 602 of FIG. 1 is at an angle of ninety degrees to the FOV 610. It can be seen that the pixels near the center of the FOV 610 have the highest intensity.

A second curve 630 shows measured EL image data values representative of an EL image along an axis on the FOV 610 of FIG. 12, when the insertable instrument 602 of FIG. 1 is at an angle of seventy-five degrees to the FOV 610. A third curve 632 shows measured EL image data values representative of an EL image along an axis on the FOV 610 of FIG. 12, when the insertable instrument 602 of FIG. 1 is at an angle of sixty degrees to the FOV 610. A fourth curve 634 shows measured EL image data values representative of an EL image along an axis on the FOV 610 of FIG. 12, when the insertable instrument 602 of FIG. 1 is at an angle of forty-five degrees to the FOV 610.

The center of the FOV 610 is indicated by a line 636 in FIG. 12A. A line 638 passes through the peaks of the curves 628-634. The departure of the line 638 from the line 636 indicates that, as the angle of the insertable instrument 602 to the FOV 610 becomes more grazing, the peak magnitude (i.e., intensity) of the EL image moves to the right. Furthermore, it can be seen that the pixel intensity varies greatly across the FOV 610 at any one angle.

Referring now to FIG. 12B, a three dimensional graph 640 includes a first axis 642 having units of image width in units of pixels associated with a charge coupled device, for example, the charge coupled device 28 of FIG. 1, which is used to generate FL image data 36 representative of an image of fluorescent light. The graph 640 also includes a second axis 644 having units of angle in degrees, wherein the angle corresponds to the angle 608 of FIG. 12. The graph 640 also includes a third axis 646 in units of pixel intensity in units of counts per second, which is equivalent to the above described intensity-per-second value, described above in conjunction with FIG. 6.

A first curve 648 shows measured FL image data values representative of an FL image along an axis on the FOV 610 of FIG. 12, when the insertable instrument 602 of FIG. 1 is at an angle of ninety degrees to the FOV 610. It can be seen that the pixels near the center of the FOV 610 have the highest intensity.

A second curve 650 shows measured FL image data values representative of an FL image along an axis on the FOV 610 of FIG. 12, when the insertable instrument 602 of FIG. 1 is at an angle of seventy-five degrees to the FOV 610. A third curve 652 shows measured FL image data values representative of an FL image along an axis on the FOV 610 of FIG. 12, when the insertable instrument 602 of FIG. 1 is at an angle of sixty degrees to the FOV 610. A fourth curve 654 shows measured FL image data values representative of an FL image along an axis on the FOV 610 of FIG. 12, when the insertable instrument 602 of FIG. 1 is at an angle of forty-five degrees to the FOV 610.

The center of the FOV 610 is indicated by a line 656 in FIG. 12B. A line 658 passes through the peaks of the curves 648-654. The departure of the line 658 from the line 656 indicates that, as the angle of the insertable instrument 602 to the FOV 610 becomes more grazing, the peak magnitude (i.e., intensity) of the FL image moves to the right. Furthermore, it can be seen that the pixel intensity varies greatly across the FOV 610 at any one angle.

Referring now to FIG. 12C, a three-dimensional graph 660 includes a first axis 662 having units of image width in units of pixels associated with a charge coupled device. The graph 660 also includes a second axis 664 having units of angle in degrees, wherein the angle corresponds to the angle 608 of FIG. 12. The graph 660 also includes a third axis 666 having units of pixel intensity in non-dimensional units.

A curve 668 is generated by dividing the curve 648 of FIG. 12B (i.e., the FL image) by the curve 628 of FIG. 12A (i.e., the EL image). Similarly, a curve 670 is generated by dividing the curve 650 of FIG. 12B by the curve 630 of FIG. 12A. A curve 672 is generated by dividing the curve 652 of FIG. 12B by the curve 632 of FIG. 12A. A curve 674 is generated by dividing the curve 654 of FIG. 12B by the curve 634 of FIG. 12A.

The first curve 668 shows corrected FL image data values (i.e., pixel intensity values) representative of a corrected FL image along an axis on the FOV 610 of FIG. 12, when the insertable instrument 602 of FIG. 1 is at an angle of ninety degrees to the FOV 610. The second curve 670 shows corrected FL image data values representative of a corrected FL image along an axis on the FOV 610 of FIG. 12, when the insertable instrument 602 of FIG. 12 is at an angle of seventy-five degrees to the FOV 610. The third curve 672 shows corrected FL image data values representative of a corrected FL image along an axis on the FOV 610 of FIG. 12, when the insertable instrument 602 of FIG. 12 is at an angle of sixty degrees to the FOV 610. The fourth curve 674 shows corrected FL image data values representative of a corrected FL image along an axis on the FOV 610 of FIG. 1, when the insertable instrument 602 of FIG. 12 is at an angle of forty-five degrees to the FOV 610.

It can be seen that all of the curves 668-674 are nearly flat, which is indicative of corrected images according the above-described technique that have substantially the same intensity across the image within a field of view.

Furthermore, it can be seen that all of the curves 668-674 achieve approximately the same average pixel intensity. Therefore, the images taken at a variety of angles 608 (FIG. 12) have the same apparent intensity and appearance for the same fluorochrome concentration.

Figure 13:
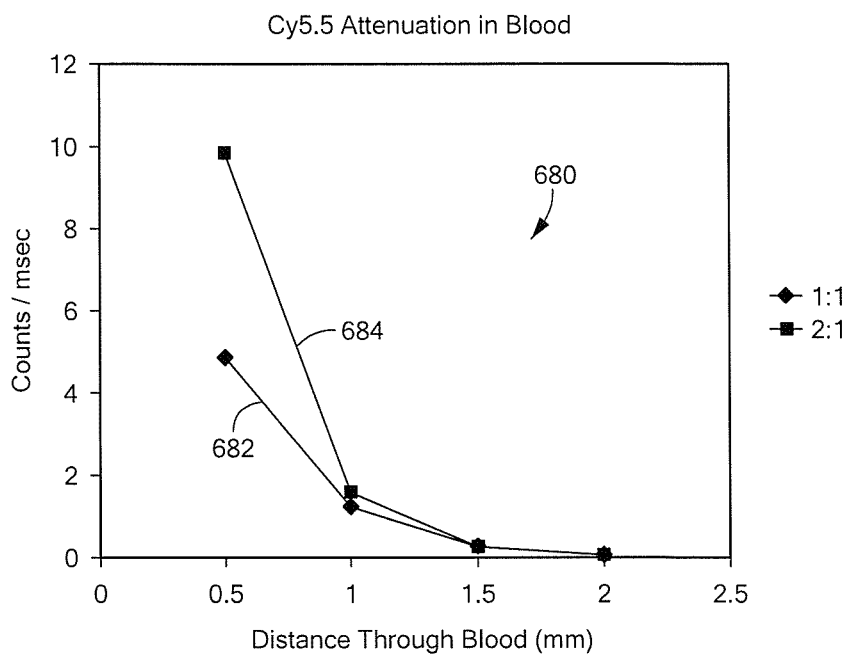
FIG. 13 is a graph showing a relation between imaging distance through blood and image intensity for a Cy5.5 fluorochrome for uncorrected images of fluorescent light.
Figure 13A:
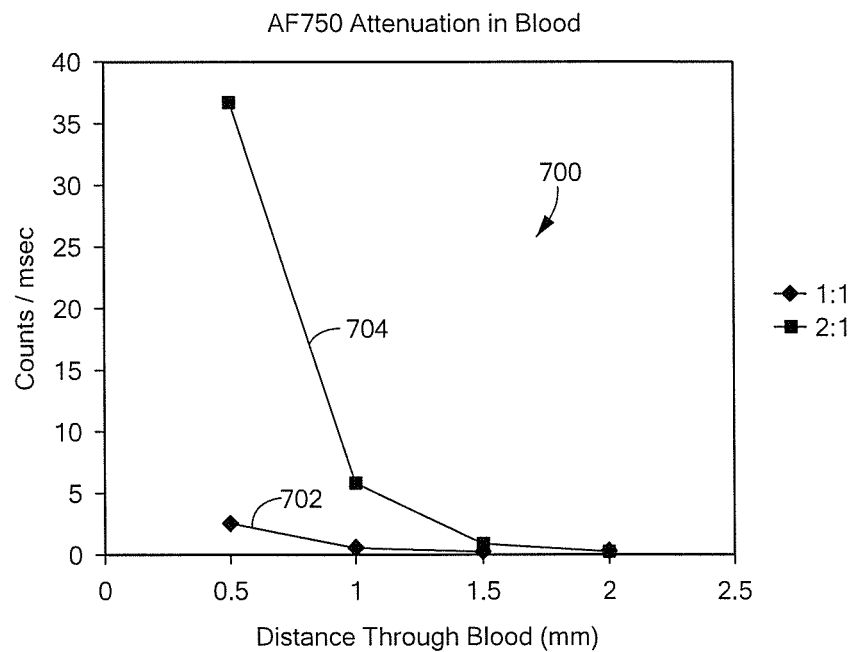
FIG. 13A is a graph showing a relation between imaging distance though blood and image intensity for an AF750 fluorochrome for uncorrected images of fluorescent light.
Figure 13B:
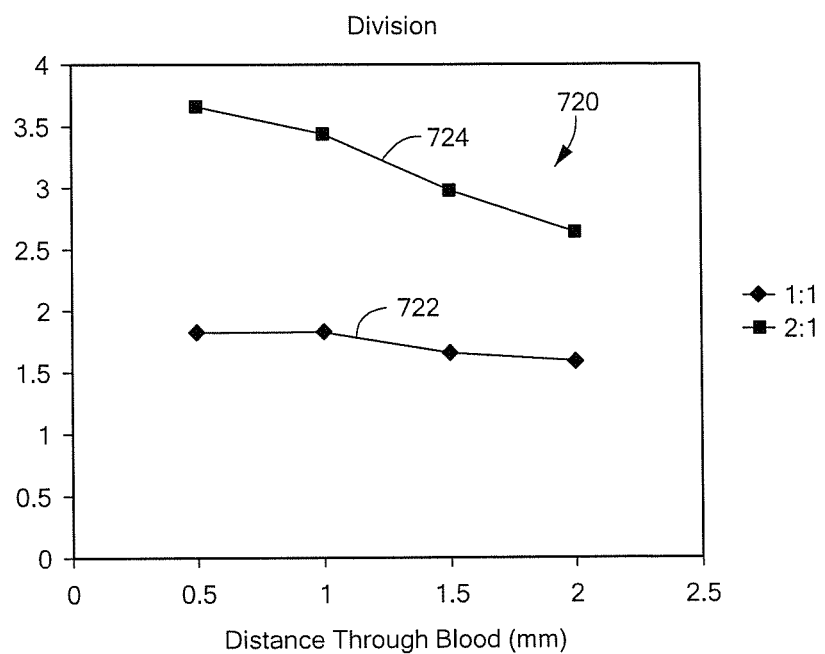
FIG. 13B is a graph showing relation between imaging distance through blood and image intensity for corrected images of fluorescent light in accordance with techniques described herein.

FIGS. 13-13B show that the above-described FL image correction techniques can also provide improved FL images when the image is taken through a diffuse medium, for example, blood. In particular, the correction techniques of FIG. 6A can be used to combine two uncorrected FL images, rather than an uncorrected FL image with an EL image as described in conjunction with FIG. 6. The two uncorrected FL images make use of two different fluorochromes in the same biological tissue being imaged, in order to generate two uncorrected FL images, which are combined to generate a corrected FL image.

Referring first to FIG. 13, a graph 680 includes a horizontal axis in units of imaging distance (i.e., distance from an insertable instrument to a biological issue being imaged with blood in the separating distance) in units of millimeters. A vertical axis has units of pixels intensity in units of counts per millisecond, which is similar to the above described intensity-per-second value described above in conjunction with FIG. 6A. It should be understood from FIG. 6A that in order to achieve the intensity-per-second values, FL image data values are divided or otherwise combined with an exposure time value associated with the image.

A first curve 682 shows a relationship between intensity-per-second values of a average pixel intensity-per-millisecond value in an ROI of an uncorrected FL image associated with a Cy5.5 fluorochrome (a first wavelength) having a ratio of AF750 fluorochrome to Cy5.5 fluorochrome of 1:1 for distances through blood of 0.5, 1.0, 1.5 and 2.0 millimeters. A second curve 684 shows a relationship between intensity-per-second values of an average pixel intensity-per-millisecond value in an ROI of an uncorrected FL image associated with a Cy5.5 fluorochrome (a first wavelength) having a ratio of AF750 fluorochrome to Cy5.5 fluorochrome of 2:1 for distances through blood of 0.5, 1.0, 1.5 and 2.0 millimeters.

It should be apparent that the curves 682, 684 are indicative of an undesirable rapid loss of intensity as a greater distance of blood separates the insertable instrument and the biological tissue being imaged.

Referring now to FIG. 13A, a graph 700 includes a horizontal axis in units of imaging distance (i.e., distance from an insertable instrument to a biological issue being imaged with blood in the separating distance) in units of millimeters. A vertical axis has units of pixels intensity in units of counts per millisecond, which is similar to the above described intensity-per-second value described above in conjunction with FIG. 6A. It should be understood from FIG. 6A that in order to achieve the intensity-per-second values, FL image data values are divided or otherwise combined with an exposure time value associated with the image.

A first curve 702 shows a relationship between intensity-per-second values of an average pixel intensity-per millisecond in an ROI of an uncorrected FL image associated with an AF750 fluorochrome (a second wavelength) having a ratio of AF750 fluorochrome to Cy5.5 fluorochrome of 1:1 for distances through blood of 0.5, 1.0, 1.5 and 2.0 millimeters. A second curve 704 shows a relationship between intensity-per-second values of an average pixel intensity-per-millisecond value in an ROI of an uncorrected FL image associated with an AF750 fluorochrome (a second wavelength) having a ratio of AF750 fluorochrome to Cy5.5 fluorochrome of 2:1 for distances through blood of 0.5, 1.0, 1.5 and 2.0 millimeters.

It should be apparent that, like the curves 682-686 of FIG. 13, the curves 702, 704 are indicative of an undesirable rapid loss of intensity as a greater distance of blood separates the insertable instrument and the biological tissue being imaged.

Referring now to FIG. 13B, a graph 720 includes a horizontal axis in units of imaging distance (i.e., distance from an insertable instrument to a biological issue being imaged with blood in the separating distance) in units of millimeters. A vertical axis has units of pixels intensity in non-dimensional units.

A first curve 722 is generated by dividing, or otherwise combining, the first curve 702 of FIG. 13A with the first curve 682 of FIG. 13. A second curve 724 is generated by dividing, or otherwise combining, the second curve 704 of FIG. 13A with the second curve 684 of FIG. 13.

It can be seen that both of the curves 722, 724 are more nearly flat than the uncorrected curves 682, 684 and 702, 704 of FIGS. 13 and 13A, respectively, which is indicative of corrected FL images according the above-described technique that have substantially the same intensity irrespective of distance through blood from the insertable instrument to a biological tissue. It should, however be recognized from the differences between the curves 722-724 that the pixel intensities in the corrected FL images remain indicative of fluorochrome concentrations.

Figure 14:
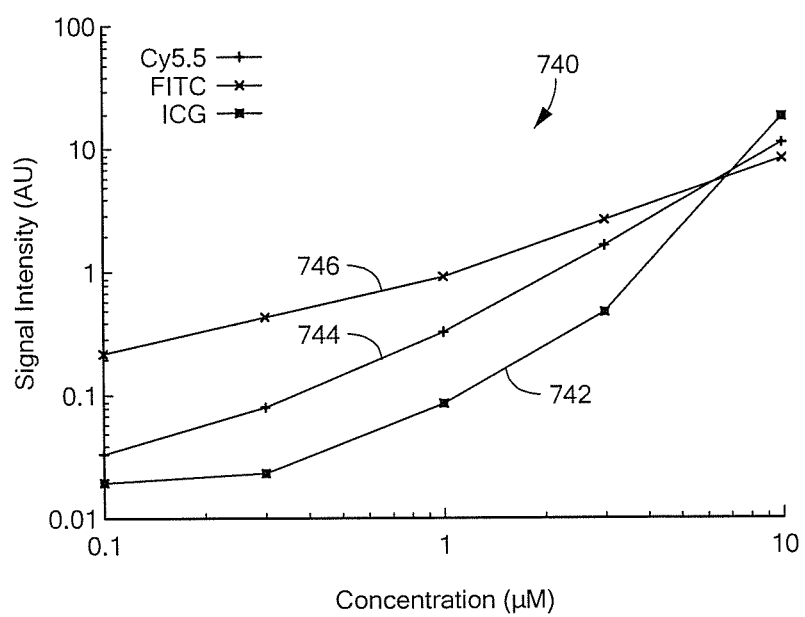
FIG. 14 is a graph showing a relation between molecule concentration and associated fluorescent light intensity for three different fluorochromes.

Referring now to FIG. 14, a graph 740 includes a horizontal axis in logarithmic units of fluorochrome concentration in units of micromolar and a vertical axis in logarithmic units of pixel intensity (not intensity-per-second) in arbitrary units, when the fluorochromes are images with an imaging device, for example, a charge coupled device.

Curve 742 shows a measured relationship between fluorochrome concentration and resulting pixel intensity for an Indo-Cyanine Green (ICG) fluorochrome. Curve 744 shows a measured relationship between fluorochrome concentration and resulting pixel intensity for a Cyanine 5.5 (Cy5.5) fluorochrome. Curve 746 shows a measured relationship between fluorochrome concentration and resulting pixel intensity for a Fluorescein isothiocyanate (FITC) fluorochrome. The process described in conjunction with FIG. 8 can be used to generate one or more of the curves 742-746.

It should be evident that colors can be assigned to predetermined concentration ranges. For example, a first color can be assigned to a range of 0.1 to 0.5 micromolar, a second color can be assigned to a range of 0.5 to 1.0 micromolar, a third color can be assigned to a range of 1.0 to 5.0 micromolar, a fourth color can be assigned to a range of 5.0 to 10.0 micromolar. However, other numbers of concentration ranges with other limits can be assigned to other numbers of colors.

The curves 742-746 can be used to identify pixel intensity ranges corresponding to the selected concentration ranges. Therefore, as discussed above in conjunction with block 360 of FIG. 7 or block 384 of FIG. 7A, an FL image, which is in gray scale, can be converted to a false color image according to molecule concentrations.

Having the relationships represented by the curves 742-746, a fluorescent light image can be false colored according to molecule concentration, once the FL image data is obtained.

Current endoscopic and catheter-based systems may have dramatic variability in fluorescence image pixel intensity values per unit time from frame to frame during tissue evaluation. The variability is due, in part, to signal intensity dependence upon angle and distance of an insertable instrument relative to a biological tissue being imaged. The variability in some cases may exceed the image to background image ratio of a fluorochrome, especially for targeted fluorochromes that often have a higher background image than activatable fluorochromes, and thus a lower image to background image ratio. In these instances in particular, accuracy of diagnosis can be decreased by the risk of false positive signals from normal tissue that is close to the device and false negative signals from pathological lesions that are farther from the insertable instrument. Therefore, there is a large unmet need for quantifying fluorescence intensity, which would markedly increase the clinical utility of catheter and endoscopic systems for diseases detection using molecularly targeted fluorochromes. An additional important benefit would be the ability to further characterize disease based upon quantitative assessment of fluorochrome activation or target binding, e.g., molecule concentration.

The above-described systems and techniques provide correction of raw FL images on a pixel by pixel basis, and on an image by image basis, in real-time as images are acquired, first by dividing pixel intensity values in acquired images by an exposure time associated with each respective image to provide intensity-per-second image data. Then the intensity-per-second FL image data can be divided by a gray scale image intensity-per second of a spatially aligned and concurrently acquired image of excitation light to provide corrected FL image data.

In other embodiments, the division of the two intensity-per-second images to generate a corrected image can be replaced with other mathematical functions. For example, other possible functions include division of the square root (e.g., square root of the FL intensity-per-second divided by the EL intensity-per-second), division by the square (e.g., FL intensity-per-second divided by the EL intensity-per-second squared), etc.

The corrected FL images remain properly exposed regardless of how close or how far the insertable instrument is from a biological tissue being imaged and regardless of the angle of the insertable instrument relative to the biological tissue. Furthermore, image intensity does not vary substantially across the field of view.

As described above, the above-described corrected FL images can be used to quantitatively measure signal intensity in a region of interest in any image of a collection of images taken in real time (or in non-real time). Because the corrected FL images are generally invariant in signal intensity with respect to distance and angle of an insertable instrument relative to a biological tissue, corrected images taken in real time (or in non real time) can be used in combination to provide a continuous dynamic image display in real time that can quantitatively depict image intensity or, in some embodiments, a quantitative concentration of fluorescent probes as the insertable instrument is moved in the body.

A quantitative aspect, i.e., image display of as concentrations as described above in conjunction with FIG. 8, can be applied to both activatable and targeted fluorescent imaging fluorochromes. Moreover, because of the invariance of images with respect to the insertable instrument position relative to the biological tissue, quantitative temporal studies are possible. For example, receptor blockade evaluation to determine optimal drug dosing could be quantitatively followed in colonic lesions using a fluorescently labeled drug analog in the same patient pre and post therapy. Likewise, vascular changes could be followed over time after anti-angiogenic therapy by the quantitative assessment of fluorescently labeled blood pool agents. Additionally, initial characterization of lesions may be possible by the use of quantitative assessment of protease activity, which has been shown in numerous cases over the last decade and a half to correlate with tumors' ability to invade and metastasize.

The methods described here are applicable to any fluorescent imaging systems, however they are particularly applicable to systems that move relative to a biological tissue being imaged, such as hand held fluorescent imaging devices or other intra-operative devices for larger area assessments.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An imaging system, comprising:
   an excitation light source adapted to direct excitation light at a tissue and adapted to excite fluorescent light from the tissue;
   a first light detector adapted to generate a first image of the tissue having a first plurality of pixel intensity values associated with a first exposure time;
   a second light detector adapted to generate a second image of the tissue having a second plurality of pixel intensity values associated with a second exposure time;
   an image correction processor coupled to the first and second light detectors and adapted to combine each one of the first pixel intensity values with the first exposure time to provide first intensity-per-second values, adapted to combine each one of the second pixel intensity values with the second exposure time to provide second intensity-per-second values, and adapted to combine the second intensity-per-second values with the first intensity-per-second values to provide a corrected image of the tissue having corrected pixel intensity values.

2. The imaging system of claim 1, further comprising an image re-scaling processor coupled to the image correction processor and coupled to receive a plurality of images, each image within the plurality of images having a respective pixel intensity value consisting of a first number of digital bits, and further adapted to convert, concurrently with receipt of each image of the plurality of images, each one of the images to a respective image having respective pixel intensity values consisting of a second different number of digital bits.

3. The imaging system of claim 2, wherein the re-scaling of each image within the plurality of images is generated in accordance with a respective scaling factor, and wherein each respective scaling factor selected in accordance with a percentage-of-histogram-area value associated with a histogram of pixel intensity values within a region of interest of the image within the plurality of images.

4. The imaging system of claim 2, wherein the re-scaling of each image within the plurality of images is generated in accordance with a respective scaling factor, and wherein each respective scaling factor is selected in accordance with a largest pixel intensity value within a region of interest of the image within the plurality of images.

5. The imaging system of claim 2, wherein at least one image within the plurality of images is an image of fluorescent light emitted from a tissue, wherein the image of the fluorescent light is a grayscale image, and wherein the imaging system further comprises an image coloring processor adapted to convert the image of the fluorescent light to a false color image.

6. The imaging system of claim 1, further, comprising:
   an intensity-to-concentration mapping processor coupled to the image correction processor and adapted to generate a map of pixel intensity values to respective concentrations of a chemical compound within a tissue; and
   an image coloring processor coupled to the image-to-intensity mapping processor and adapted to apply the map to a grayscale image to generate a false color image according to the concentrations concurrently with receipt of the grayscale image.

7. The imaging system of claim 1, further comprising a calibration processor coupled to the first and second light detectors, wherein the calibration processor comprises:
   a region of interest processor adapted to identify a region of interest in the first image and in the second image, and
   a registration processor adapted to spatially align the region of interest of the first image with the region of interest of the second image, wherein the image correction processor is adapted to divide each one of the first pixel intensity values in the region of interest of the first image by the first exposure time to provide first intensity-per-second values, adapted to divide each one of the second pixel intensity values in the region of interest of the second image by the second exposure time to provide second intensity-per-second values, and adapted to divide the second intensity-per-second values by the first intensity-per-second values to provide a corrected image of the tissue in the region of interest having corrected pixel intensity values.

8. The imaging system of claim 1, wherein the first light detector is adapted to generate a first plurality of images, each image within the first plurality of images having a respective exposure time, and the second light detector is adapted to generate a second plurality of images, each image within the second plurality of images having a respective exposure time, wherein the imaging processor further comprises:
   a first exposure processor coupled to the first light detector and adapted to dynamically adjust the respective exposure times associated with each image within the first plurality of images; and
   a second exposure processor coupled to the second light detector and adapted to dynamically adjust the respective exposure times associated with each image within the second plurality of images.

9. The imaging system of claim 1, further, comprising:
   an image combining processor adapted to receive a secondary image from another type of imaging system and to combine the corrected image with the secondary image to provide a combined image concurrently with the generation of the corrected image.

10. The imaging system of claim 9, wherein the another type of imaging system is a selected one of a magnetic resonance imaging system, a computer tomography system, an x-ray system, a fluoroscopy system, or a positron emissions tomography system.

11. The imaging system of claim 1, further comprising:
    a first image capture processor configured to capture the first image from the first light detector, wherein the first image capture processor comprises a first exposure processor configured to dynamically adjust the exposure time associated with the first image by adjusting the first light detector;
    a second image capture processor configured to capture the second image from the second light detector, wherein the second image capture processor comprises a second exposure processor configured to dynamically adjust the exposure time associated with the second image by adjusting the second light detector, wherein the exposure time associated with the first image is adjusted independently from the exposure time associated with the second image; and
    a memory coupled to the first and second image capture processors and configured to receive and store the first and second images and configured to receive and store the respective exposure times.

12. The imaging system of claim 1, further comprising an imaging instrument coupled to the first and second light detectors, wherein the corrected pixel intensity values in the corrected image are generally invariant with respect to a distance and angle between the imaging instrument and the tissue.

13. The imaging system of claim 1, wherein the image correction processor is adapted to divide each one of the first pixel intensity values by the first exposure time to provide first intensity-per-second values, adapted to divide each one of the second pixel intensity values by the second exposure time to provide second intensity-per-second values, and adapted to divide the second intensity-per-second values by the first intensity-per-second values to provide a corrected image of the tissue having corrected pixel intensity values.

14. The imaging system of claim 1, wherein the first pixel intensity values are color pixel intensity values and the second pixel intensity values are grayscale pixel intensity values, and wherein the image correction processor is further adapted to convert the color pixel intensity values to other grayscale pixel intensity values.

15. The imaging system of claim 1, wherein the first image is generated in accordance with the excitation light reflecting from the tissue, and wherein the second image is generated in accordance with the fluorescent light.

16. The imaging system of claim 1, wherein the fluorescent light is generated by an autofluorescence of the tissue.

17. The imaging system of claim 1, wherein the fluorescent light has a first fluorescent light component having a first spectral band and a second fluorescent light component having a second spectral band, and wherein first image is generated in accordance with the first fluorescent light component, and wherein the second image is generated in accordance with the second fluorescent light component.

18. The imaging system of claim 1, further comprising a calibration processor coupled to the first and second light detectors, wherein the calibration processor comprises:
 a region of interest processor adapted to identify a region of interest in the first image and in the second image, and
 a registration processor adapted to spatially align the region of interest of the first image with the region of interest of the second image, wherein the image correction processor is adapted to divide each one of the first pixel intensity values in the region of interest of the first image by the first exposure time to provide first intensity-per-second values, adapted to divide each one of the second pixel intensity values in the region of interest of the second image by the second exposure time to provide second intensity-per-second values, and adapted to divide the second intensity-per-second values by the first intensity-per-second values to provide a corrected image of the tissue in the region of interest having corrected pixel intensity values.

19. The imaging system of claim 1, wherein the first light detector is adapted to generate a first plurality of images, each image within the first plurality of images having a respective exposure time, and the second light detector is adapted to generate a second plurality of images, each image within the second plurality of images having a respective exposure time, wherein the imaging system further comprises:
 a first exposure processor coupled to the first light detector and adapted to dynamically adjust the exposure times associated with each image within the first plurality of images; and
 a second exposure processor coupled to the second light detector and adapted to dynamically adjust the exposure times associated with each image within the second plurality of images.

* * * * *